United States Patent
Alves De Carvalho et al.

(10) Patent No.: US 10,726,155 B2
(45) Date of Patent: Jul. 28, 2020

(54) GENOME QUERY HANDLING

(71) Applicant: CBRA GENOMICS, S.A., Cantanhede (PT)

(72) Inventors: André Dias Alves De Carvalho, Moinhos (PT); Helder Lameiras Sousa, Condeixa-A-Nova (PT); Nuno Manuel De Castro Arantes-Oliveira, Gibirita-Paco de Arcos (PT); Bruno Flávio Nogueira De Sousa Soares, Oporto (PT); Ana Sofia Pedrosa Pinto, Cantanhede (PT); Pedro Jorge Pereira Lopes, Ilhavo (PT)

(73) Assignee: CBRA GENOMICS, S.A., Cantanhede (PT)

( * ) Notice: Subject to any disclaimer, the term of this patent is extended or adjusted under 35 U.S.C. 154(b) by 164 days.

(21) Appl. No.: 16/062,575

(22) PCT Filed: Dec. 2, 2016

(86) PCT No.: PCT/EP2016/079686
§ 371 (c)(1),
(2) Date: Jun. 14, 2018

(87) PCT Pub. No.: WO2017/102390
PCT Pub. Date: Jun. 22, 2017

(65) Prior Publication Data
US 2018/0365446 A1 Dec. 20, 2018

(30) Foreign Application Priority Data
Dec. 16, 2015 (PT) .......................... 109034

(51) Int. Cl.
*G06F 21/62* (2013.01)
*G06F 16/951* (2019.01)
(Continued)

(52) U.S. Cl.
CPC ........ *G06F 21/6254* (2013.01); *G06F 16/951* (2019.01); *G06F 21/602* (2013.01);
(Continued)

(58) Field of Classification Search
CPC .................................................. G06F 21/6254
See application file for complete search history.

(56) References Cited

U.S. PATENT DOCUMENTS 6,397,224 B1    5/2002   Zubeldia et al.
9,928,379 B1*   3/2018   Hoffer ................. G06F 21/6245
(Continued)

FOREIGN PATENT DOCUMENTS

WO    2004/031922 A2    4/2004

OTHER PUBLICATIONS

International Search Report and Written Opinion for related International Application No. PCT/EP2016/079686, dated Mar. 3, 2017; 11 pages.

Primary Examiner — Simon P Kanaan
(74) Attorney, Agent, or Firm — Procopio, Cory, Hargreaves & Savitch LLP

(57) ABSTRACT

A method of processing a query on a genome to produce a report is disclosed. The method comprises receiving a first secret, a second secret and a query request over a communications network during a first communications session and storing a proxy value associated with the query request in a database. The first secret is used to determine a genome key enabling access to genome data stored in the database and associated with the first secret. The proxy value and a query key are associated using the second secret such that the query key can only be found using both the proxy value and the second secret. An association is stored between the genome key and the query key in the database and the first and second secrets are deleted subsequent to determining the genome key and associating the proxy value and query key, during or at the end of the first communications session, to ensure anonymity. The genome is identified using the (Continued)

genome key and a query associated with the query request is applied to the identified genome to generate a report, which is stored in the data base in association with the query key, whereby the report can be accessed in the database using the query key. Subsequent to storing the report, the association between the genome and query keys is deleted to further ensure anonymity. Also disclosed are methods of generating queries and loading genomes, as well as systems, servers, computer program products and computer readable media implementing the above.

20 Claims, 14 Drawing Sheets

(51) Int. Cl.
*G16B 50/00* (2019.01)
*G16H 10/60* (2018.01)
*G06F 21/60* (2013.01)
*H04L 9/08* (2006.01)

(52) U.S. Cl.
CPC ............ *G16B 50/00* (2019.02); *G16H 10/60* (2018.01); *H04L 9/0861* (2013.01)

(56) References Cited

U.S. PATENT DOCUMENTS

2014/0372149 A1 12/2014 Friese et al.
2015/0379303 A1* 12/2015 LaFever .............. G06F 21/6218
 726/28
2018/0365446 A1* 12/2018 Alves De Carvalho .....................
 G06F 21/6254

* cited by examiner

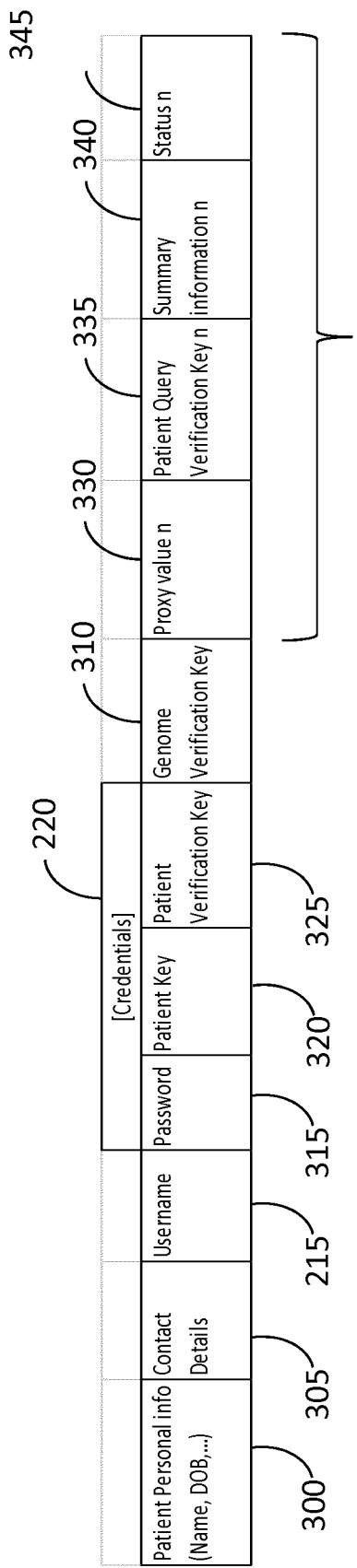
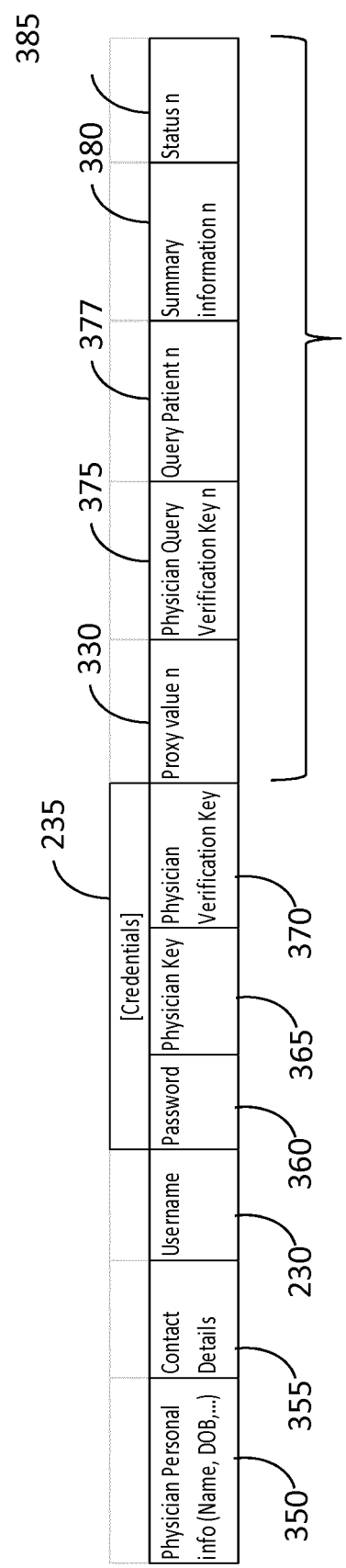
Figure 3a
Figure 3b

GENOME QUERY HANDLING

CROSS-REFERENCE TO RELATED APPLICATIONS

This application is a U.S. National Stage entry of PCT Application No: PCT/EP2016/079686 filed Dec. 2, 2016, which claims priority to Portuguese Patent Application No. 109034, filed Dec. 16, 2015, the contents of which are incorporated herein by reference.

The present disclosure relates to the handling of genome queries, in particular although not exclusively the handling of genome queries submitted by a physician together with a patient.

BACKGROUND

Personalised medicine based on the analysis of a patient's genome is showing great promise in increasing the efficacy of treatments and enabling new treatments previously not possible. Currently, a typical process involves the submission of a DNA containing sample from a patient to a genomic laboratory, where the patient's genome is fully or partially sequenced to answer a specific question, facilitating a physician making diagnostic or treatment decisions. Such queries involve looking for certain features or markers in the genome, such as mutations and repeated sequences of DNA in certain genes, abnormal chromosome numbers, the presence or absence of certain genes, gene duplication, among others.

In the current state of the art, genome sequencing needs to be performed every time a genetic test is requested due to privacy and anonymity concerns. Additionally, the formulation of a genome query result requires significant specialist knowledge that many physicians do not possess. Even when physicians have relevant specialist knowledge, elaboration of answers to a genome query requires specialist geneticists, typically a scarce resource. The need for sequencing the whole genome or part of it every time a condition/disease has to be tested, and the level of specialisation required both to perform the analysis and to interpret the results mean that obtaining answers to genomic queries is a time-consuming and costly process which limits access to a personalised medicine.

SUMMARY

To address the shortcomings inherent in the current state of the art, it would be desirable to provide a framework for automatically processing genome queries in a way that is less time-consuming, while still addressing any concerns regarding privacy and anonymity of sensitive genome data.

In a first aspect, there is provided a method of processing a genome query to produce a report. A first secret, a second secret and a query request are received over a communications network, for example at a server, during a first communications session. A proxy value associated with the query request is stored in a database. The query request may also be stored in the database.

The first secret is used to determine a genome key, which enables access to genome data, associated with the first secret, stored in the database. The first secret may belong to a patient and may, for example, be generated from a physical token belonging to the patient, for example when the patient inserts the physical token into a client computer connected over the communications network. This may involve generating the first secret from data on the physical token, for example using a one-way function. Thus, when the first secret belongs to a patient, the genome is associated with the patient via the first secret, or more generally with the owner of the first secret. The association between the genome key and the genome data may be due to the way the genome data was stored in the database in association with the genome key, for example as described below.

Using the first secret to determine the genome key may comprise evaluating a function, for example a one-way function, combining a candidate genome key in the database with the first secret and comparing the result with a genome verification key associated with the first secret. If there is a match, the associated genome key has been found, otherwise the process is repeated with another candidate genome key until a match is found (of course, the evaluation can first be made of all genome key, followed by looking for a match). The genome verification key may be associated with the first secret by being stored in a user profile that is accessible with credentials including the first secret. While the user profile may be accessible using the first secret, the first secret is not stored with the user profile, to ensure that the genome data cannot be accessed with only the user profile without receiving the first secret. As used herein, credential may generally include the described secrets and other information such as usernames and/or passwords to provide two or more factor credentials. However, the credentials may in some embodiments consist of only the secret, for example the first secret, and reference to "credentials" is thus to be construed as including the case of single factor credentials.

The proxy values and a query key are associated using the second secret so that the query key can only be found with the proxy value by using both the proxy value and the second secret. The second secret may be owned by a physician treating the patient and submitting the query request together with the patient. For example, the second secret may be generated from data on a physical token belonging to the physician and may be generated at the client computer from the data, for example using a one-way function. In that way, a physician and patient may submit a query request together by each inserting their physical token into the client computer for the submission of the query request.

The proxy value and query key may be associated by computing a query verification key as a function, for example a one-way function, combining the proxy value, query key and second secret and storing the query verification key in the database. The query verification key may be stored in the data base in association with the second secret and the proxy value. For example, the query verification key and proxy value may be stored in a user profile accessible with credentials including the second secret. While the user profile may be accessible using the second secret, the second secret is not stored in the user profile to prevent access to the query without receipt of the second secret.

It will be appreciated that the respective functions used to calculate the different verification keys (genome verification function combining a genome key and the first secret; query verification function combining a query key, a proxy value and the second secret; further query verification function combining a query key, a proxy value and the first secret) will differ in the inputs they take to generate the corresponding verification key but may otherwise be the same, i.e. implementing the same operation, for example the same one-way function, or one or more of the respective functions may each implement a different respective operation to generate each respective type of verification key.

Once the genome and query keys have been found and/or generated, an association is stored between the genome and query keys in the database and the first and second secrets are deleted, for example responsive to associating the genome and query keys or at the end of the first communications session. The association may be direct and/or explicit, or it may be indirect, for example via the stored query or another stored database entry. Since the genome and query keys can only be found using the first secret, once the first and second secrets are deleted, the association between the genome and query keys and the patient and/or physician cannot be established by tracing back from the genome and query keys, thereby safeguarding anonymity of the data associated with these keys. For example, where the genome/query keys are found using a calculation involving one of the secrets to match against the verification keys, without the secret present, the database contains unrelated sets of genome/query (database access) keys on the one hand and verification keys on the other hand. A pair of verification and database access keys can only be matched up in the presence of the secret, keeping a user linked in the database to the verification key anonymous in light of the database access key and hence keeping the data associated with the database access key anonymous. Anonymity can further be enhanced by the use of one-way functions as described above.

To process the genome query, the genome data is identified using the genome key and the query associated with the query request (associated with a query key) is applied to the identified genome data to generate a report. The report is stored in the database in association with the query key. In this way, the report can be accessed in the database using the query key. Subsequent to storing the report in this way, the association between the genome and query keys is deleted. In this way, anonymity is further enhanced, since the genome cannot be traced back from the report without receiving again the first and second secrets.

Thus, advantageously, by using database access keys that require secrets, which are not kept on the server, to be found, the anonymity of the patient (or other owner of the first secret and genome data) is safeguarded, preventing an association of the genome data and/or reports with the patient without receipt of the first secret. By the specific handling of the creation and deletion of the various associations in the database, a process is enabled which allows the genome data to be obtained once, stored in a way that addresses anonymity and privacy concerns, and used multiple times to answer various genomic queries. Thus, a significant bottleneck in the application of personalised medicine, as discussed above, is eliminated. Further, the use of two secrets in the way described above ensures that the owner of the second secret, for example a physician, cannot run a genomic query without the consent of the owner of the first secret, but is able to retrieve the resulting report in the absence of the owner of the first secret, for example to prepare for a consultation with the owner of the first secret. Thus, the described way of handling genomic queries enables, for example, a physician to obtain reports on genomic queries in an efficient manner that respects patient privacy and anonymity and facilitates access to personalised medicine for the patient.

By virtue of associating the query key with the proxy value (via the second secret), the proxy value uniquely identifies each query. Proxy values may be generated in any suitable way providing unique proxy values, for example incrementing a counter or randomly attributing unique identifiers, for example using universally unique identifiers (see https://en.wikipedia.org/wiki/Universally_unique_identifier). The proxy values may be pre-generated and stored ready for use when required, or may be generated in response to the receipt of a genome query.

In a second, subsequent communications session, in embodiments relating to retrieval of the generated report, the second secret is received again over the communications network and used with the proxy value to find the query key. Subsequent to finding the query key, the second secret is deleted, during or at the end of the second communication session. Using the query key the report is identified and sent over the communications network during the second communications session.

Finding the query key may involve evaluating the function used to compute the query verification key for the proxy value and a candidate query key in the data base and comparing the result with the query verification key to find a match between the result and the query verification key, as described above for the genome verification key.

In embodiments in which the verification keys are stored in association with a secret, for example in a user profile accessible with credentials including the secret, the comparison between function values and verification keys can be made directly for the relevant verification key associated with the relevant secret. Alternatively, a query could be run for all combinations of database access and verification keys (or all database and verification keys that pertain to the same type of object, e.g. query or genome), with a match indicating that both the verification key and the database access key are associated with the secret in question. Yet other embodiments do not rely on verification keys but rather generate database access keys from the respective secrets using a corresponding one-way function, for example generating a genome key from a first secret using a first one-way function and generating a query key from a combination of a second secret and a proxy value using a second one-way function (of course the first and second one-way functions could be the same save for, for example, combining the input with a genome signifying string for the first one-way function and a query signifying string for the second one-way function).

In some embodiments, a plurality of proxy values are stored together in the database so that they are accessible using credentials including the second secret. For example, the proxy values may be stored in a user profile accessible with the credentials. In this way all proxy values associated with queries generated by the owner of the second secret, and hence all the associated queries can be accessed. The proxy values may be pre-generated and associated with the profile in advance. Alternatively, the association between the profile and the proxy values may be generated in response to receiving the query request, independently of whether the proxy value itself has been pre-generated or has been generated in response to the query request.

During the second communications session, then, summary information for the queries/reports associated with the stored together proxy values are sent to the client device to enable a user to select a report to retrieve. For example, the summary information for each report may be associated with a corresponding identifier which is sent from the client computer over the communications network in response to selection of a report/summary information, while an association between this identifier and the proxy value (or query key) corresponding to the report is stored in the server to enable the retrieval of the report, for example as outlined above. At the server, a proxy value corresponding to the identifier is then retrieved and used to find the corresponding query key as described above, which is then used to retrieve the corresponding report. The retrieved report is then sent to the client where the owner of the second secret can review it.

In some embodiments, when the first secret is used to access the corresponding genome, contact information associated with the owner of the first secret is retrieved and is used to send a message indicating that the first secret has been used to access the genome. In that way, an owner of the first secret, for example a patient, will receive a notification each time the first secret is received by the server, providing further protection against unauthorised use of the first secret. In some embodiments, the contact information is stored in association with the genome verification key (where applicable), for example in a user profile accessible with credentials including the first secret, in which the genome verification key is also stored.

It will be appreciated that the respective functions used to calculate the different verification keys (genome verification function combining a genome key and the first secret; query verification function combining a query key, a proxy value and the second secret; further query verification function combining a query key, a proxy value and the first secret) will differ in the inputs they take to generate the corresponding verification key but may otherwise be the same, i.e. implementing the same operation, for example the same one-way function, or one or more of the respective functions may each implement a different respective operation to generate each respective type of verification key.

In a second aspect, there is provided a method of populating a genomic database which optionally may be in addition or an alternative to the first aspect. A first secret is received over a communications network during a communications session and used with a genome key to generate a genome verification key, enabling access to genome data once this is stored in the database. The genome verification key is generated such that the genome key can be found with the genome verification key only using both the first secret and the genome verification key. The first secret is deleted subsequent to generating the genome verification key, for example at the end of the communication session or immediately once the key has been generated. The genome verification key may be stored in a user profile accessible using credentials that may include the first secret. In this way, the owner of the first secret cannot be traced back from the genome key, as discussed above. The genome key can then be sent to the owner of the first secret to send to a genome provider designated by the owner of the first secret (or may be sent directly to the genome provider) to allow the sequenced genome, once received from the genome provider, to be made accessible via the genome key while protecting the anonymity of the owner of the first secret. This may involve loading the genome into the database and storing it in association with the genome key. Alternatively, the genome provider may store the genome at their end such that it is accessible with the genome key, as long as they do not associate details of the owner of the first secret with the genome key. The genome can then be accessed at the genome provider using the genome key when needed.

In some embodiments, the genome key can be generated from the first secret using a one-way function that is stored (or identified) by the user profile (enabling retrieval by passing the secret through the one-way function as discussed above) instead of generating and storing a verification key.

The genome is then received together with the genome key and stored in the database in association with the genome key. From this point on, the genome can be identified for retrieval using the first secret to find the genome key, as described above.

In the first and second aspects and their embodiments, clinical data associated with the owner of the genome may be stored in the database in association with the genome key. This enables retrieval of the clinical data in a similar manner as described above. Further, by establishing an association between the genome data and corresponding clinical data via the genome key, correlations between clinical data and genome data can be analysed while respecting the privacy and anonymity of the genome owner. It will, of course, be understood that the genome and clinical data may be associated in other ways than by the genome key, for example by a separate key common to both the genome and clinical data, or in any other way.

Likewise, as mentioned above, the first secret may be associated with the patient and the second secret may be associated with a physician. The first and second secrets may have been derived from a respective physical token at the client computer, for example using a one-way function applied to data on the token at the client computer. The first and second secrets are then transmitted over the communications network and used as described above. Typically, in particular in embodiments were the first and second secrets belong to, respectively, a patient and a physician, the first and second secrets are not the same. However, in some embodiments, the first and second secrets may be one and the same secret, so that the owner of the secret can both load his genome into the database and submit and retrieve genome queries, using the secret as described above. For example a patient can manage the entire process described above without assistance from a physician. Even when the first and second secrets are not the same, the owner of the first and second secrets may be the same person, for example the patient. In this case, the owner, for example the patient, would manage the whole process, albeit using two secrets and, for example, two corresponding physical tokens.

In some embodiments, access to generated reports associated with respective query keys using the first secret is enabled. Specifically, respective further query verification keys may be computed using the query keys and associated proxy values, this time together with the first rather than the second secret. These query verification values are then stored in a user profile associated with the owner of the first secret (or accessible using credentials comprising the first secret), together with associated query summary information and other information such as query status. This provides the owner of the first secret with the option of carrying out some or all actions the owner of the second secret can carry out. For example, the owner of the first secret, such as a patient, may in this way have independent access to the reports generated, so that they can be made available to a third party, for example a physician who is not the owner of the second secret if the owner of the first secret wishes to obtain a second opinion.

In embodiments where keys are generated from the secrets using a one-way function for later retrieval, further keys may be generated from the first secret, corresponding to keys generated from the second secret and providing access to queries or groupings of query keys.

In any of the above aspects and embodiments, applying a one-way function to an input may comprise concatenating the input with a random string and operating on the result with a one-way function. Irrespective of whether the input is combined with a string or not, the one-way function may be a cryptographic hash function, for example SHA-256. The string may be numeric, alphanumeric or characters only and may be specific and unique to the one-way function in question, that is a first string for the first one-way function, a second string for the second one-way function, and so on. More generally, it will be understood that a one-way function as used here is a function for which it is hard or in practice impossible to find the input given the output and it will be appreciated that many such functions are well known in the art.

Further, in any of the above aspects and embodiments, the genome query may comprise instructions to look for certain chromosome numbers, chromosomal coordinate ranges, gene names, accession numbers, keywords or terms describing genome data from specialised databases such as but not limited to Genbank, Uniprot, EBI or NCBI, variant identification numbers, literature references, variant pathogenicity prediction, protein functional effects prediction. Additionally, any or more of the preceding may be associated with a disease, condition or drug such as but not limited to Cardiomyopathy, Diabetes, Thrombophilia, Colorectal cancer therapy, Alzheimer's Disease, Glaucoma, Rheumatoid Arthritis, Cystic fibrosis, Hemochromatosis, Pediatric Deafness, in areas such as but not limited to Cardiology, Endocrinology, Haematology, Gastroenterology, Neurology, Ophthalmology, Rheumatology, Pulmonology, Internal Medicine or Paediatrics.

For the avoidance of doubt, where reference is made to associations between different items in the database, for example keys such as the genome and query key, these associations may be explicit and direct, storing for example both keys as a database record, or they may be indirect, for example by associations with one or more common items, from which the items in question can be associated with each other, that is given one item, the other item can be found.

BRIEF DESCRIPTION OF THE DRAWINGS

Specific embodiments are now described by way of example, with reference to the accompanying drawings, in which:

FIG. 3a illustrates information stored in a patient profile in the private portion of the database;

FIG. 3b illustrates information stored in a physician profile in the private portion of the database;

SPECIFIC DESCRIPTION

Figure 1:
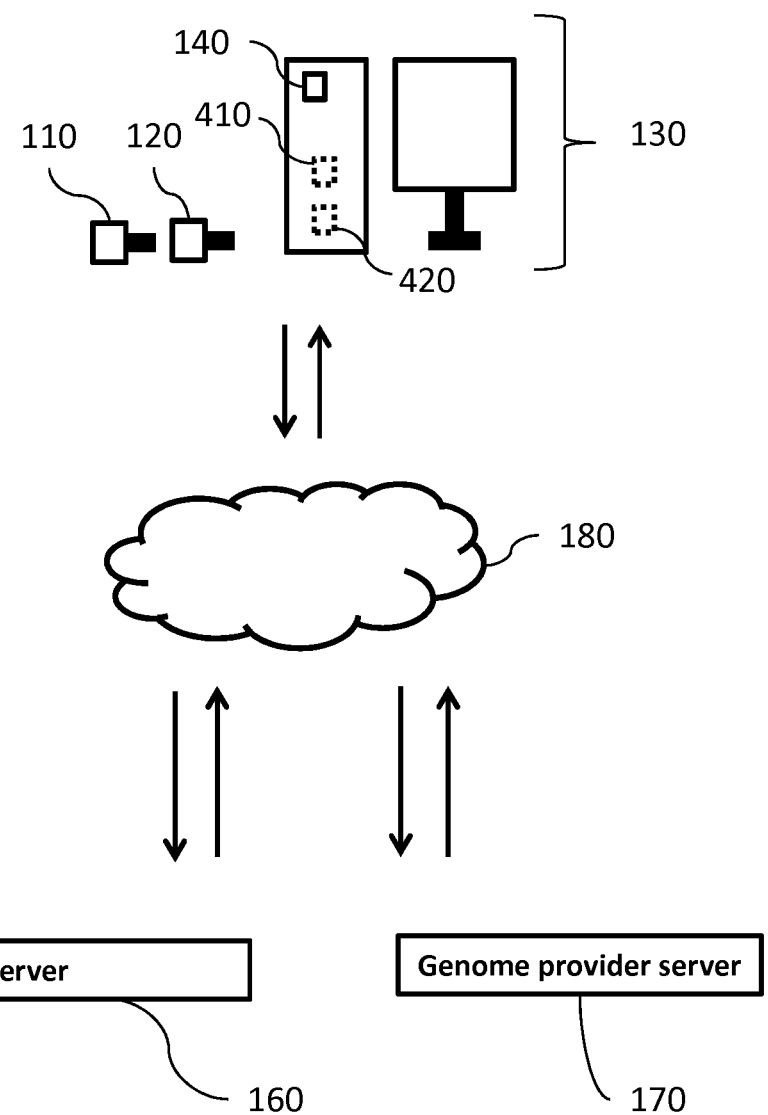
FIG. 1 illustrates a client/server system for implementing processes described below.

With reference to FIG. 1, a client computer 130, typically located at a physician's office, comprises a reader 140 for reading physical tokens 110, 120 in addition to conventional computer hardware, such as an appropriate processing infrastructure, input devices and a display. The physical tokens belong to, respectively, a patient and a physician and each carry a digital signature, for example a random string, unique to the owner. Respective first and second secrets 410, 420 can be generated from the digital signatures, as described below. The client computer 130 is in communication with a server 160 configured to process genome queries, as described below, over a communications network 180, for example the internet. Communications over the communications network 180 may be over secure, encrypted channels, for example using SSL or other protocols. The server 160 implements or has access to a genome database holding genome data for processing, as will be described below. The client computer 130 and/or server 160 are in communication with a genome provider server 170 for providing genome data to the server 160.

Figure 2:
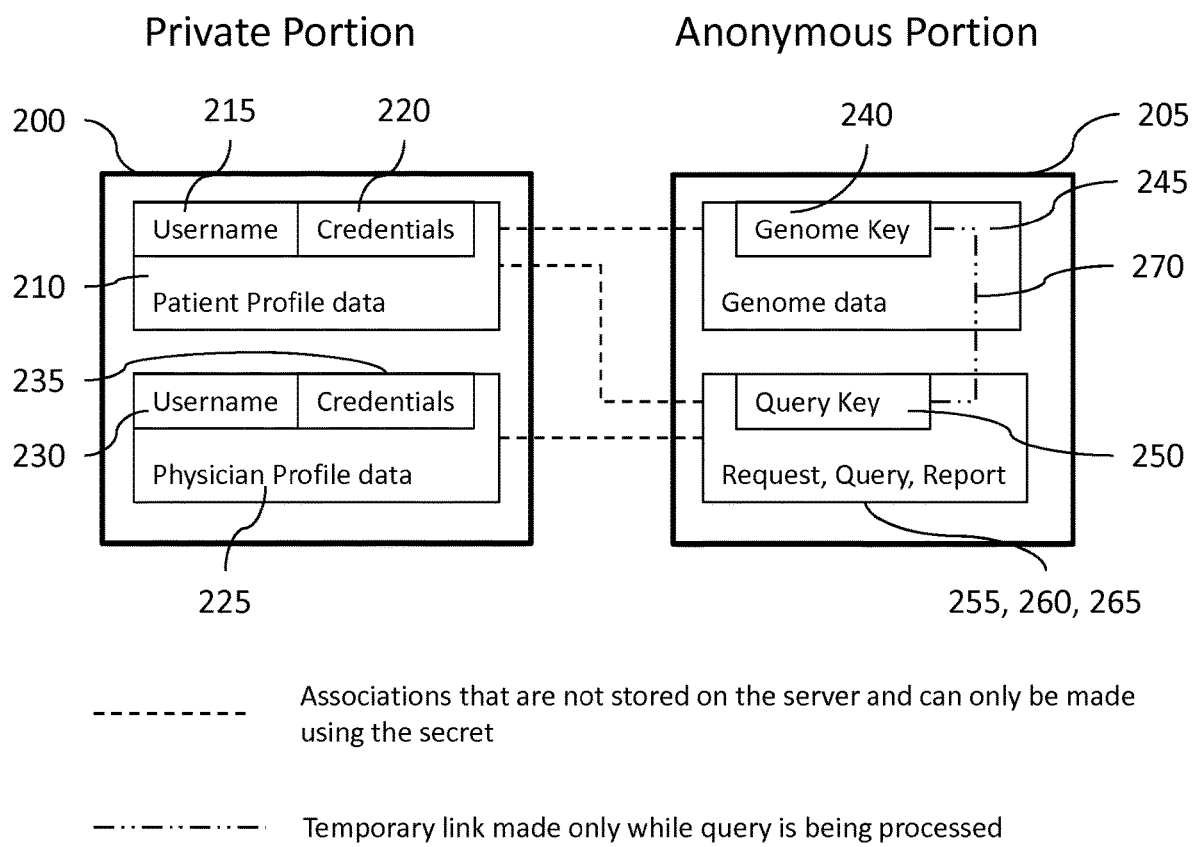
FIG. 2 illustrates a database having a private portion and an anonymous portion.

With reference to FIG. 2, a database stored at the server 160 holds data to enable processing of queries on patients' genomes, submitted by patients together with their physician, and comprises a private portion 200 and an anonymous portion 205. The private portion 200 comprises a patient profile 210 for each patient comprising a patient username 215, patient credentials 220 and profile data described below. The private portion 200 additionally comprises a physician profile 225 for each physician comprising a physician username 230, physician credentials 235 and profile data described below. The anonymous portion 205 comprises a genome key 240 stored in association with genome data 245 and profile data described below. The anonymous portion 205 additionally comprises a query key 250 stored in association with a query request 255, a query 260 and a report 265 for each stored query. A temporary link 270 between the genome key 240 and the query key 250 is stored in the anonymous portion 205 of the database to enable a query 260 to be processed by the server 160 as described below. No links are stored between the private and anonymous portions 200, 205 of the database but the profiles 210, 225 in the private portion 200 of the database contain information enabling them to be associated with keys (and hence the corresponding data) in the anonymous portion 205 in the presence of a respective secret received from the patient or physician, as the case may be, as described in detail below. The anonymous portion 205 contains no information that could be linked to the profiles in the private portion 200, to ensure anonymity.

With reference to FIG. 3a, the patient profile 210 for each patient comprises patient personal information 300, patient contact details 305, a genome verification key 310, the patient credentials 220 comprising a password 315, a patient key 320 and a patient verification key 325, and for each query a proxy value 330, a patient query verification key 335, a query summary information 340 and a report status 345, all of which will be described in some detail below. The query related information need only be stored in embodiments where access for reports is enabled for patients as well as for physicians.

With reference to FIG. 3*b*, the physician profile 225 for each physician comprises physician personal information 350, physician contact details 355, physician credentials 235 comprising a password 360, a physician key 365 and a physician verification key 370, and for each query a proxy value 330, a physician query verification key 375, a query patient 377, a query summary information 380 and a report status 385 which will be described in some detail below. It will be noted that the physician and physician verification key (as well as the patient and patient verification key mentioned above with reference to FIG. 3*a*) are stored in the profile in order to enable the first (second) secret to be verified as part of the credentials used during the log in process. It will be apparent that many other techniques that equally avoid storing the secrets in the profiles can be employed instead and that, in some embodiments, the secrets can be omitted from the credentials used to log in to the profile and only be used to make the association between the verification key(s) in the profile(s) and corresponding database key(s) in the anonymous part of the database.

Figure 4A:
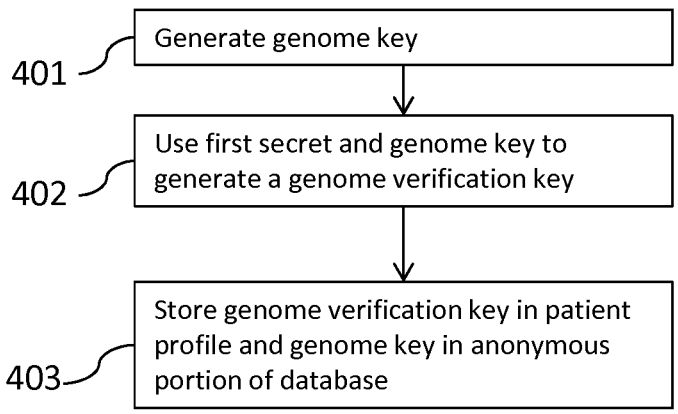
FIG. 4a illustrates a process for indirectly associating a patient profile with a genome key by way of a first secret owned by a patient.

As mentioned above, no links are stored in the database between the private and anonymous portions but associations between these can be made using secrets belonging to the patient or the physician. With reference to FIG. 4*a*, a process for associating the patient profile 210 and the genome key 240 is now described. At step 401 the server 160 generates the genome key 240. In some embodiments, the server 160 generates the genome key 240 by applying a one-way function to a first secret 410 owned by the patient and further described below in combination with a random value to generate a secure key, and subsequently applies a one-way function to a combination of the first secret 410 and the secure key to generate the genome key 240. Specifically, in some embodiments the random value is a 64-character alphanumeric string. However, in some embodiments, the genome key may be pre-computed and step 401 may be skipped.

At step 402, the server 160 uses the first secret 410 and the genome key 240 to generate the genome verification key 310. In some embodiments, the server 160 generates the genome verification key 310 by applying a one-way function to the genome key 240 and the first secret 410 concatenated together. At step 403, the server 160 stores the genome verification key 310 in the patient profile 210 of the private portion 200 of the database, and stores the genome key 240 in the anonymous portion 205 of the database (unless the genome key is pre-computed and already stored).

Figure 4B:
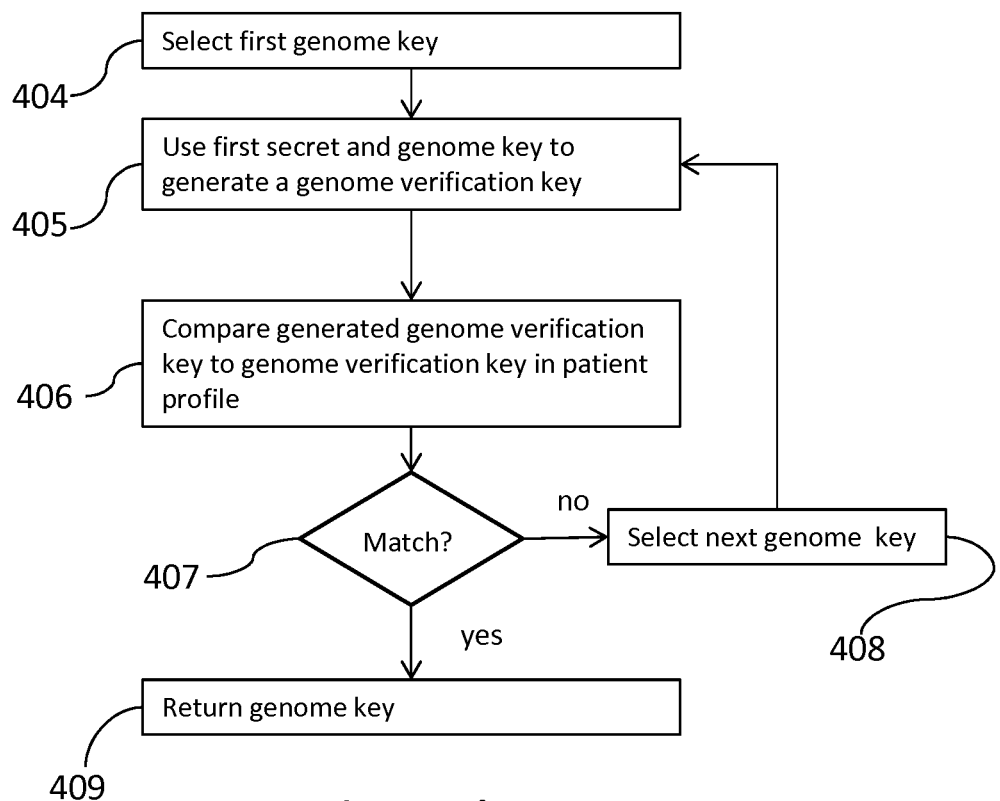
FIG. 4b illustrates a process for finding a genome key using a genome verification key and a first secret owned by a patient.

With reference to FIG. 4*b*, a process for finding the genome key 240 using the genome verification key 310 and the first secret 410 is now described. At step 404, the server 160 selects a first genome key 240 stored in the anonymous portion 205 of the database, and then at step 405 using the first secret 410 and the selected genome key 240, the server 160 generates a genome verification key 310. At step 406, the server 160 compares the generated genome verification key of step 405 to the genome verification key 310 stored in the patient profile 210. Then at step 407, the server 160 checks if the two verification keys match. If the genome verification key generated in step 405 does not match the genome verification key 310 stored in the patient profile 210, the server 160 selects a next genome key 240 in the database at step 408 and loops back to step 405 to repeat the process for the next genome key 240. If the genome verification key generated in step 405 matches the genome verification key 310 stored in the patient profile 210, the server 160 returns the genome key 240 as the associated genome key at step 409. In this way, the genome data 245 stored in association with the genome key 240 may be identified using the corresponding genome verification key 310 and the first secret 410.

Figure 5A:
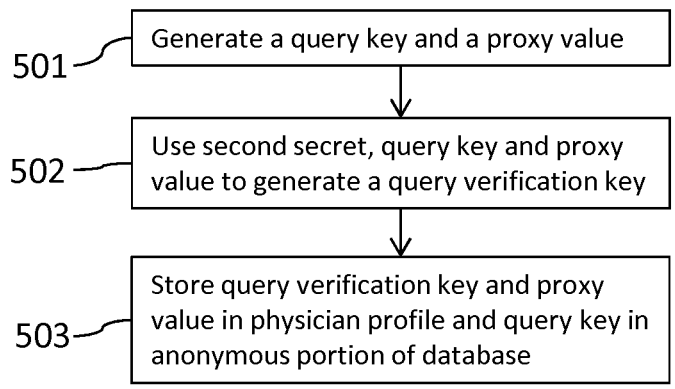
FIG. 5a illustrates a process for indirectly associating a physician profile and a query key by way of a second secret owned by a physician.

With reference to FIG. 5*a*, a process for associating the physician profile 225 and the query key 250 is now described. At step 501, the server 160 generates the query key 250 and the proxy value 330. In some embodiments, the server 160 generates the query key 250 by applying a one-way function to the second secret 420 in combination with a random value to generate a secure key, and subsequently applies a one-way function to a combination of the second secret 420 and the secure key to generate the query key 250. Specifically, in some embodiments the random value is a 64-character alphanumeric string. However, in some embodiments, the genome key may be pre-computed and step 501 may be skipped.

At step 502, the server 160 generates the physician query verification key 375 using a combination of the second secret 420, the query key 250 and the proxy value 330. In some embodiments, the server 160 generates the physician query verification key 375 by applying a one-way function to the query key 250 and the second secret 420. At step 503, the server 160 stores the physician query verification key 375 and the proxy value 330 in the physician profile 225 in the private portion 200 of the database, and stores the query key 250 in the anonymous portion 205 of the database.

Figure 5B:
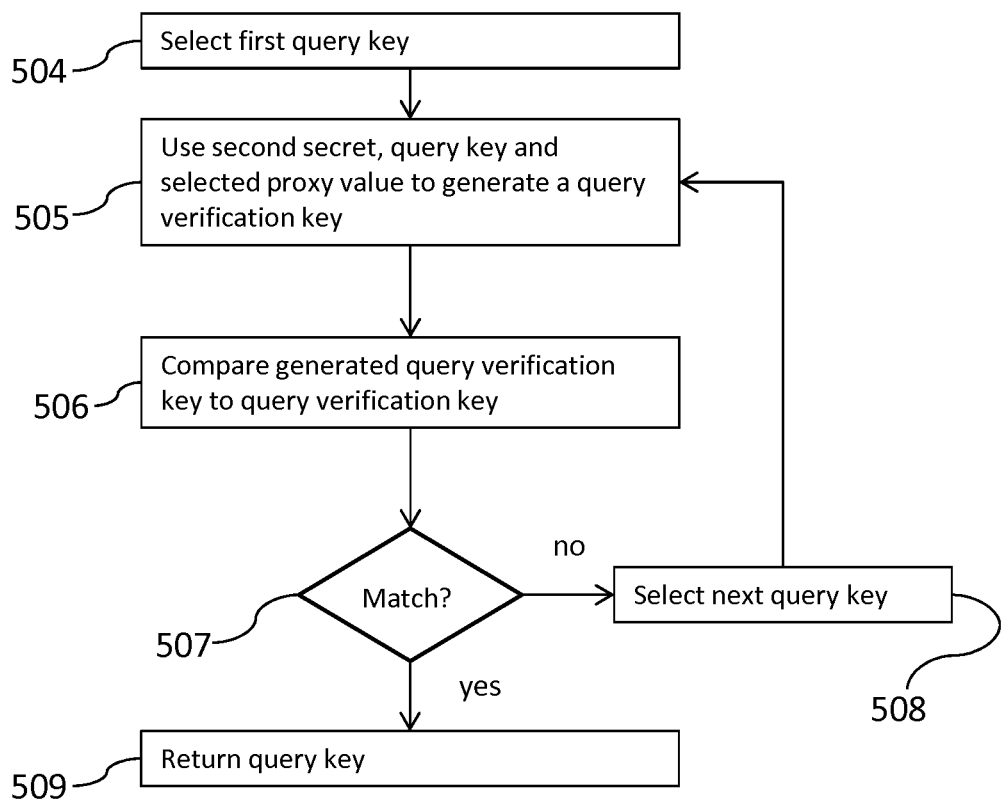
FIG. 5b illustrates a process for finding a query key using a query verification key and a second secret owned by a physician.

With reference to FIG. 5*b*, a process for finding a query key 250 using the physician query verification key 375 and the second secret 420 is now described. At step 504, the server 160 selects a first query key 250 stored in the anonymous portion 205 of the database. Then at step 505 using a combination of the second secret 420, query key 250 and a selected proxy value 330, the server 160 generates a query verification key. At step 506, the server 160 compares the generated physician query verification key of step 505 to the physician query verification key 375 stored in the physician profile 225. Then, at step 507, the server checks if the two verification keys match. If the physician query verification key generated in step 505 does not match the physician query verification key 375 stored in the physician profile 225, the server 160 selects a next query key 250 at step 508 and then loops back to step 505 to repeat the process for the next query key 250. If the physician query verification key 375 generated in step 505 matches the physician query verification key 375 stored in the physician profile 225, the server 160 returns the query key 250 at step 509.

The above description makes reference to combining certain items (e.g. a secret and a key) or to a combination of items. In some embodiments, the items are strings and combining them comprises concatenating the strings. In some embodiments, combining items further comprises applying a one-way function to the concatenated strings. For example the one-way function is a cryptographic hash in some embodiments, for example SHA1, 2 or 3. In some embodiments, concatenation of strings can be replaced with other combinations of the items before applying a one-way function to the combination.

In some embodiments where access to queries 260 and/or requests 255 associated with respective query keys 250 is to be provided to patients independently of their physician, query related data is added to the patient profile 210, as described above with reference to FIG. 3*a*, for example by using the processes described above with reference to FIGS.

5a and 5b to produce a patient query verification key 335 for the same proxy value 330 and query key (i.e. skipping step 501) using the first secret 410 instead of the second secret 420 and storing the patient query verification key 335 and proxy value 330 in the patient profile 210. The patient query verification key 335, together with the proxy value 330 and the first secret 410 can then be used to find the query key 250 as described above for the physician query verification key 375 and second secret 420 with reference to FIG. 5b.

Figure 6:
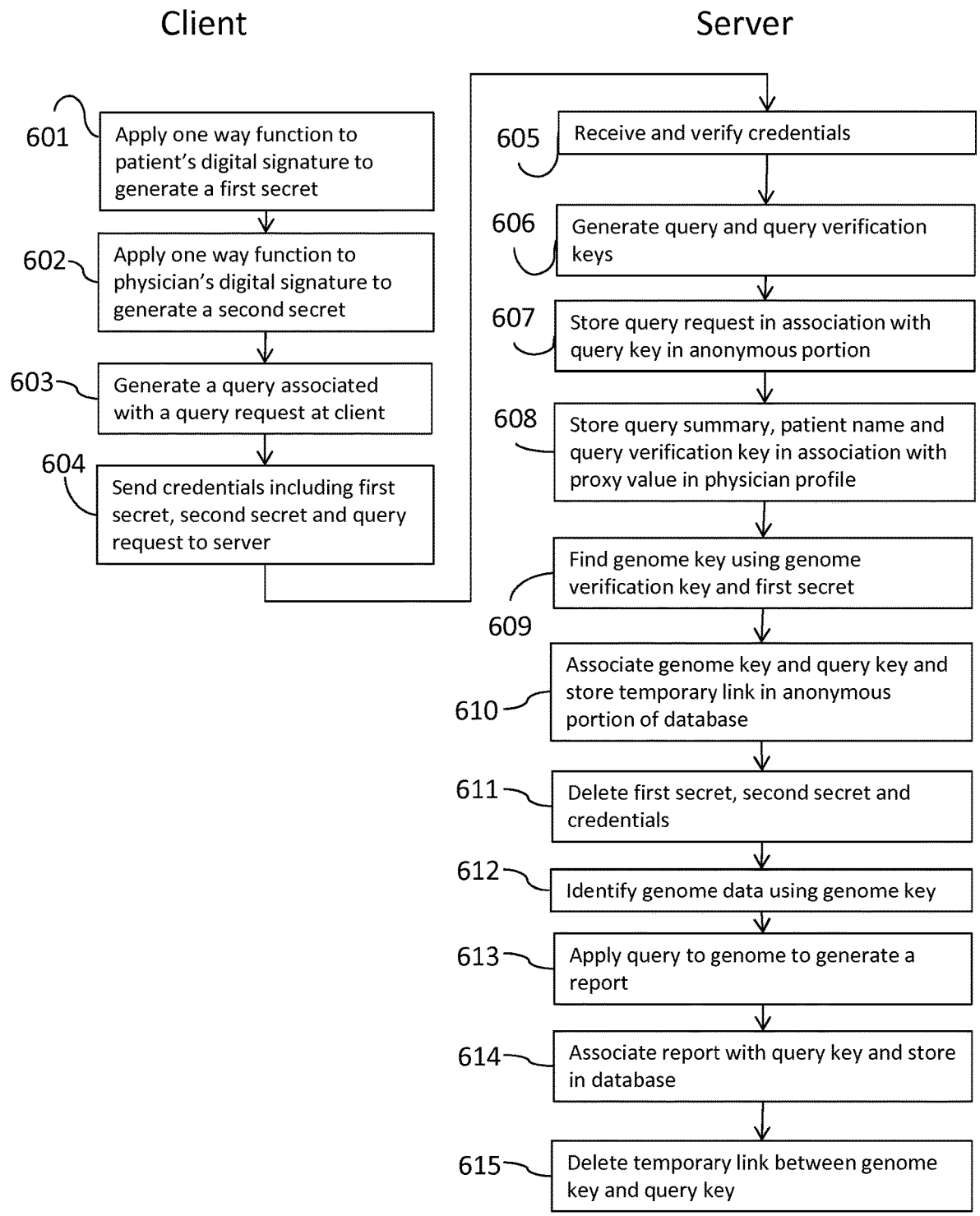
FIG. 6 illustrates a process for processing a genome query.

With reference to FIG. 6, a process during a first communications session between the client computer 130 and the server 160 to produce the report 265 is now described. The state of the genome database during this process is described below with reference to FIGS. 9a-d. During the first communications session between the client computer 130 and the server 160 the patient and physician both insert their token 110, 120 into the reader 140, either simultaneously or in sequence to submit a query request for the processing of a genome query 260.

The patient and physician log in to the client computer 130 using their respective username and password as credentials and insert their tokens in to the reader 140 at the client computer 130. At step 601, the client computer 130 reads a patient digital signature from the patient token 110 and applies a one-way function to the patient digital signature to generate the first secret 410. At step 602, the client computer 130 concurrently or sequentially reads a physician digital signature from the physician token 120 and applies a one-way function to the physician digital signature to generate the second secret 420. It will be understood that at step 601 and step 602, the client computer 130 can receive the patient token 110 and the physician token 120 in any order, and that the client computer 130 can read the patient digital signature and physician digital signature in any order. At step 603, the client computer 130 generates the query 260 associated with the query request 255. At step 604, the client computer 130 sends patient and physician credentials, including the first secret 410, second secret 420, and the query request 255 which comprises the query 260, over the communications network 180 to the server 160.

At step 605, the server 160 receives the query request 255 and query 260, as well as the patient credentials 220 and the physician credentials 235 and verifies each set of credentials against the respective profile 210, 225. At step 606, the server 160 generates the query key 250 and the physician query verification key 375 as described above (with reference to FIG. 5a).

At step 607, the server 160 stores the query request 255 and query 260 in association with the query key 250 in the anonymous portion 205 of the database and, at step 608, the server 160 stores the query summary information 380, the query patient name 377 and physician query verification key 375 in association with the proxy value 330 in the physician profile 225 in the private portion 200 of the database. It will be understood that a patient query verification key 335 can be generated in the same way as that of the physician query verification key 375 and stored in association with the proxy value 330 in the patient profile 210 in the private portion 200 of the database to enable access to the query/report by the patient, as described above.

At step 609, the server identifies the genome key 240 associated with the first secret 410 using the first secret 410 and the genome verification key 310 as described above (with reference to FIG. 4b). Then, at step 610, the server 160 creates a temporary link 270 in the anonymous portion 205 of the database associating the genome key 240 and the query key 250 to enable processing of the query on the genome. Subsequently, the first and second secrets 410, 420 are no longer needed and, at step 611, the server 160 deletes the first secret 410, the second secret 420, the patient credentials 220 and the physician credentials 235 so that the data in the private and anonymous portions 200, 205 can no longer be associated, thereby ensuring anonymity. The deletion may occur immediately when the secrets are no longer needed, or at the end of the first communications session.

At a subsequent point in time (for example once the query comes to the top of a processing queue), at step 612, the server 160 runs the query and to that end finds the genome data 245 using the temporary link 270 between the query key 250 and the genome key 240 to identify the genome key 240 and hence the genome data 245 stored in association with it. Then, at step 613, the server 160 applies the query 260 associated with the query request 255 to the found genome data 245 to generate a report 265 and at step 614, stores the report 265 in association with the query key 250.

At step 615, the server 160 deletes the temporary link 270 between the genome key 240 and the query key 250, so that the report 265 can be retrieved without risk to the patient's anonymity from an identification of the genome. At this stage, all data that may have represented a privacy risk has been removed from the server 160 and the report 265 is ready for collection.

After one or more first communications sessions as described above, the database of the server 160 comprises one or more query keys 250 and reports 265 in the anonymous portion 205 of the database and one or more query keys 250, proxy values 330 and query verification keys 375 in the physician profile 225. Thus, the one or more reports 265 are ready for collection as will now be described.

Figure 7:
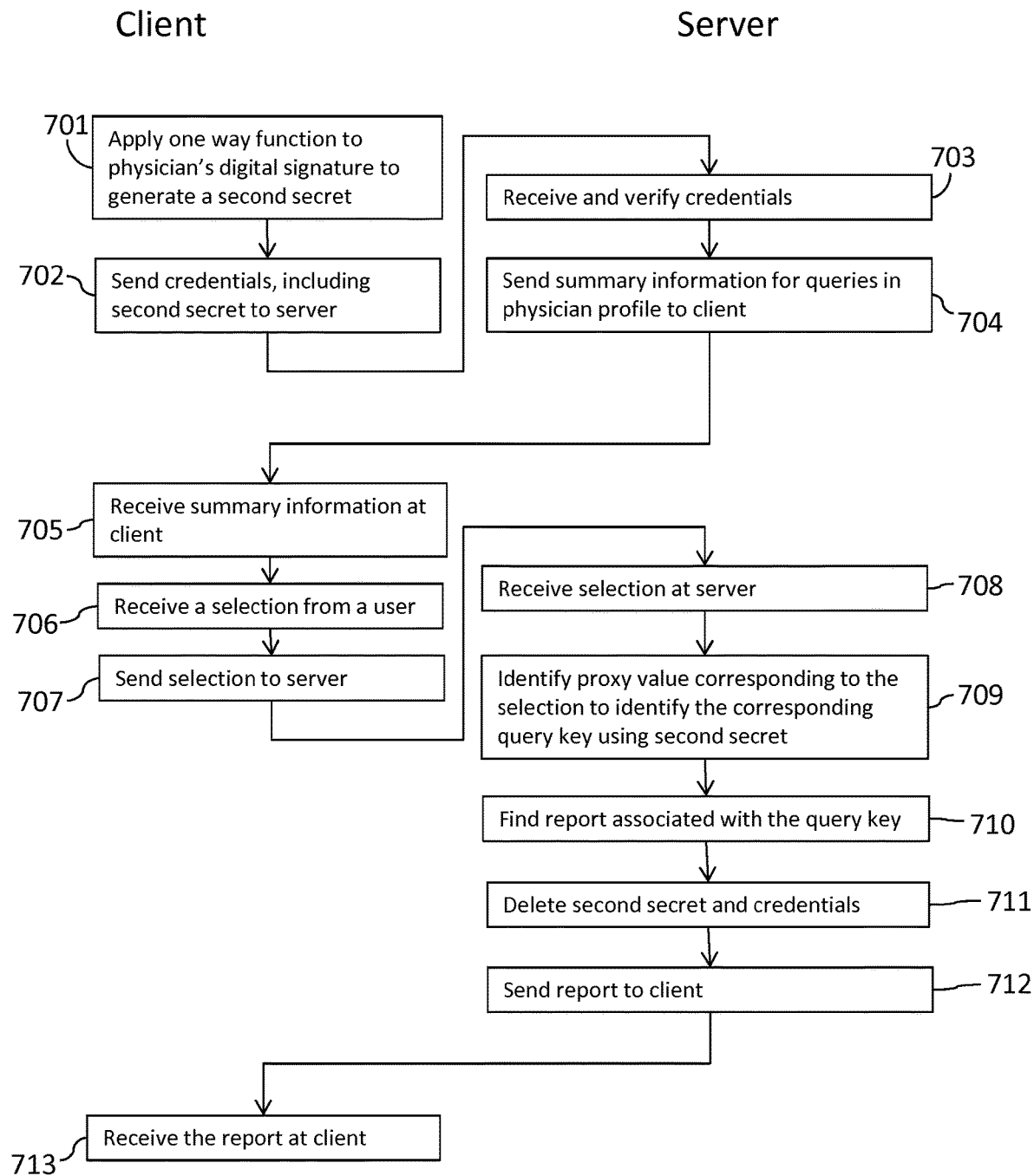
FIG. 7 illustrates a process for providing report summaries to enable selection of a report to be retrieved and for providing the selected report.

With reference to FIG. 7, a process enabling a physician to retrieve a summary of his or her reports 265 using his or her token 120 is now described. At step 701, during a second communications session between the client computer 130 and the server 160, the physician provides his or her credentials 235, including his or her token 120 to the client computer 130 and the client computer 130 reads the physician digital signature from the physician token 120 and applies a one-way function to the physician digital signature to generate the second secret 420. At step 702, the client computer 130 sends the credentials 235 including the second secret 420 over the communications network 180 to the server 160, together with a request to retrieve query summary information 380.

At step 703, the server 160 receives the credentials 235 including the second secret 420 and verifies them against the respective physician profile 225 associated with the physician username 230. Then, at step 704, the server 160 sends the summary information 380 associated with each query 260 in the physician profile 225 to the client computer 130.

At step 705, the client computer 130 receives the query summary information 380 for each query in the profile from the server 160 over the communications network 180. The query summary information 380 comprises information for use by the physician to identify his or her query requests 255 and/or the respective associated reports 265. The query summary information 380, in some embodiments, comprises the patient name, the genome query name, the query request current status indicating whether the query request 255 is pending or finished, and the query request order and delivery dates. For each processed query request 255, the query summary information 380 for each query may be used by the physician to select a corresponding one of the reports 265 for retrieval.

Having selected a report 265 to retrieve, the physician can now retrieve the selected report 265. At step 706, the physician makes a selection, selecting one or more reports 265 from the query summary information 380 for retrieval using the client computer 130 for example by selecting an item of summary information on a display screen at the client computer 130.

At step 707, the client computer 130 sends over the telecommunications network 180 to the server 160 the selection, which is received by the server 160 at step 708.

At step 709, the server 160 identifies the proxy value 330 corresponding to the selection to identify the corresponding query key 250 using the second secret 420 as described above with reference to FIG. 5b. With the correct query key 250 identified, at step 710, the server 160 finds the corresponding report 265 using the association 930. As this is no longer needed, at step 711, the server 160 deletes the second secret 420 to safeguard privacy. In some embodiments, the server 160 deletes the second secret 420 at the end of the second or third communications session. Finally, at step 712, the server 160 sends the identified report 265 to the client computer 130 over the communications network 180, and at step 713, the client computer 130 receives the report 265.

While the present system has been designed with anonymity and privacy in mind, it may sometimes be necessary or desirable to contact the patient (the owner of the genome). One example of this occurs in embodiments in which a message is sent to the patient, for example by email, each time the first secret 410 is processed to access a genome. To this end, contact details 305 are stored in the patient profile 210 and may comprise any one or more of an email address, a telephone number or any other means for contacting the owner of the first secret 410. With this information, the server 160 sends over the communications network 180 a message to the patient in response to receipt of the first secret 410. The message may comprise any one or more of an email notification, a mobile phone notification, a voicemail, SMS message or any other means of notifying the owner of the first secret 410. In this way, misuse of the first secret 410 is easier to detect, while at the same time ensuring anonymity, since the contact details 305 are associated with the patient profile 210, which cannot be associated with the genome or genome key in the absence of the first secret 410.

Figure 8:
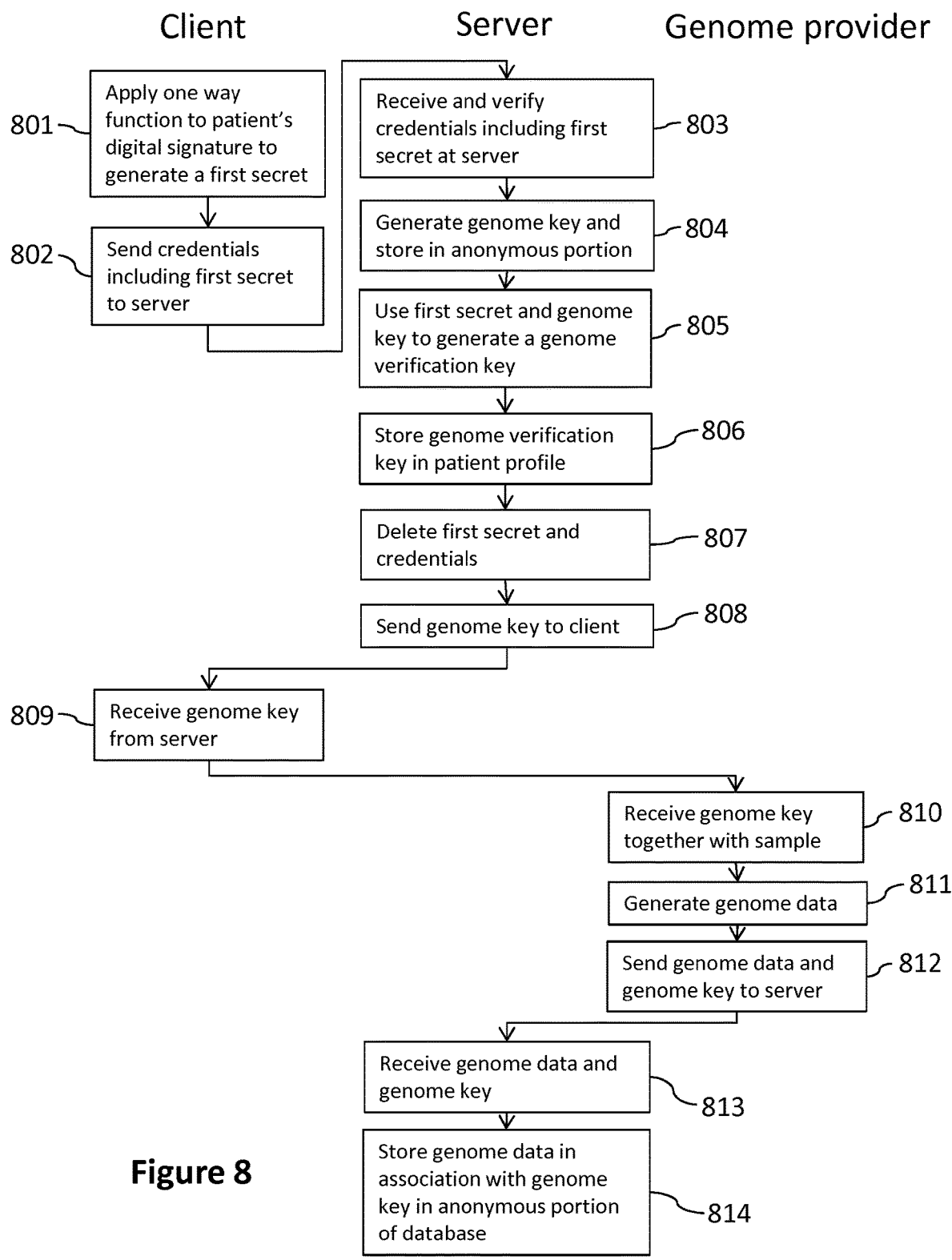
FIG. 8 illustrates a process for populating a genome database.

The above description has focused on the submission of genome queries and the retrieval of generated reports 265, accessing a database that already contains genome data 245 for the patient. With reference to FIG. 8, a process for adding genome data 245 for a patient to the database is now described. In overview, the patient (or the physician on behalf of the patient) commissions the patient's genome to be sequenced by a genome sequencing provider. The patient/physician also commissions the operator of the server 160 to host the genome data 245 in the database, and to liaise with the genome sequencing provider to obtain the genome data 245 and associate it with the genome key 240 in the database. It will be understood that, in some circumstances, the operator and genome sequencing provider may be one and the same entity or may be controlled by the same entity.

Turning now to FIG. 8, then, at step 801, during a communications session between the client computer 130 and the server 160 during which the patient credentials 220 and the patient token 110 is presented to the client computer 130, the client computer 130 reads a patient digital signature from the patient token 110 and applies a one-way function to the patient digital signature 200 to generate the first secret 410, subsequent to which, at step 802, the client computer 130 sends the patient credentials 220 including the first secret 410 over the communications network 180 to the server 160.

At step 803, the server 160 receives the patient credentials 220, including the first secret 410 from the client computer 130 over the communications network 180 and verifies the patient credentials 210 against the respective patient profile 210.

At step 804, the server 160 generates the genome key 240 as described above with reference to FIG. 4a and stores this in the anonymous portion 205 of the database. In some embodiments, the genome key 240 already exists within the anonymous portion 205 of the database. At step 805, the server 160 generates the genome verification key 310 using the genome key 240 and the first secret 410 as described above with reference to FIG. 4a. Then at step 806, the server 160 stores the genome verification key 310 in the patient profile 210 in the private portion 200 of the database. As this is no longer needed, at step 807, the server 160 deletes the patient credentials 220, including the first secret 410, to safeguard anonymity. In some embodiments, the server 160 deletes the patient credentials 220, including the first secret 410, at the end of the communications session.

Once the genome key 240 has been generated at step 804, the server 160 sends the genome key 240 over the communications network 180 to the client computer 130 at step 808, and the genome key 240 is received at the client computer 130 at step 809. The physician/patient commissions the patient's genome to be sequenced by sending to a genome sequencing provider 170 the genome key 240, a suitable sample (e.g. a mouth swab, blood sample etc.) and a request to send the sequenced genome data 245 to the operator of the server 160 together with the genome key 240.

At step 810, the genome provider 170 receives the genome key 240 together with the sample to be sequenced and generates the genome data 245 by sequencing the sample at step 811. The genome provider 170 performs DNA extraction for sequencing analysis and generates genome data 245 suitable for external processing. Then, at step 812, the genome provider 170 sends to the server 160 over the communications network 180 the genome data 245 and the corresponding genome key 240.

At step 813, the server 160 receives over the communications network 180 from the genome provider 170 the genome data 245 and genome key 240.

At step 814, the server 160 queries the database for the genome key 240 and thereby identifies where to store the genome data 245 in the anonymous portion 205 of the database. The server 160 then permanently associates the genome key 240 and the genome data 245 in the anonymous portion 205 of the database, ready for use as described above.

The above description focuses in detail on storing genome data 245 so that it is accessible in the database using the patient's secret key. Where the genome data 245 is a whole genome sequence, this will only need to be sequenced once, although the process can of course be repeated to add additional genome data 245 to the database (in the case of partial sequences, for example), in which case the process described above is modified in step 804 of FIG. 8, in that the genome key 240 is not generated for the first time but is already present when it is generated from the first secret 410. In the same way, this process can be used to associate clinical data with the genome key 240 while respecting anonymity. When clinical data is associated with genome data 245 in the database, the database can be mined for genotype-phenotype correlations without compromising anonymity and the clinical data can be used to enhance genome queries. It will, of course, be understood that the association between the clinical data and the genome data 245 need not be made via the genome key 240 but could be made using a separate key associated with the genome key 240 or genome data 245.

In the above described embodiment, the genome provider sends the genome data 245 together with the genome key 240 for storage at the server 160 or in a database maintained by the server 160. In other embodiments, the genome provider may store the genome data 245 at their end and make it accessible, using the genome key 240, to the server 160, which, consequently, does not store the genome data 245 but can access it at the genome provider when needed. Of course, as long as the genome data 245 is accessible using the genome key 240, it can be stored at any other location, for example maintained by a third party, as well. Other process variations are equally possible, for example the server 160 may send the genome key to both the client and genome provider or only to the genome provider (with the sample either being routed via the operator of the server 160 or otherwise matched with the genome key at the genome provider).

In some embodiments, it may be desirable to allow the patient to be able to access his or her report 265 without the physician, for example to discuss them with a third party. In some embodiments, this is implemented using the processes described above with reference to FIGS. 5a, 5b and 7 by replacing the second secret 420 belonging to the physician with the first secret 410 belonging to the patient, enabling access by the patient in addition to or instead of by the physician. In a similar fashion, in some embodiments, the interaction of the system is only with the patient, in which case the patient either owns the first and second physical tokens 110, 120 and the first secret 410 and second secret 420, or the first and second tokens 110, 120 and/or secrets 410, 420 can be replaced with a single token and secret combining the functions described above for the separate tokens/secrets.

The embodiments described above make reference to user profiles for the patient/physician, in which various items of data allow associations between the private and anonymous portions of the database to be made in the presence of the relevant secret. Access to the profiles has been described as two-factor, that is including both a username and a password, as well as a token-derived secret. It will be understood that single factor verification using only the secret and username is equally possible. Likewise, the profiles need not contain all of the above described information. For example, to implement core functionality, it would be sufficient if profiles included the relevant verification keys and proxy values. Even inclusion of usernames in the profiles could be optional and replaced with exhaustive querying of relevant verification keys using the relevant secret and/or proxy values, as the case may be.

The above described embodiments rely on the generation of verification keys used in database queries to identify keys in the anonymous portion of the database. However, in other embodiments, described below, keys in the anonymous portion are instead generated by respective specialised one-way functions and these embodiments thus dispense with the use of verification keys. Some such embodiments are described below. As described, these embodiments use credentials consisting only of the relevant secret, but other factors could of course be included in the credentials as well.

In what follows, embodiments using one-way functions for combined key generation and identification are described. These embodiments are now described with reference to FIGS. 9 and 10, referencing FIGS. 6 and 7 to indicate how the processes in these embodiments differ from those described above. The description below is made in terms of credentials including only the token-generated secrets described above but it will be understood that other factors can be included.

Figure 9A:
FIGS. 9a-9d illustrate a process for processing a genome query in embodiments using one-way functions for combined key generation and identification.

With reference to the process described in FIG. 6, embodiments using one-way functions for combined key generation and identification replace steps 605 to 609 with the following process. The server 160 receives the first secret 410, second secret 420 and query request 255. The state of the information stored in the database is illustrated in FIG. 9a. The server 160 stores the first secret 410, second secret 420 and query request 255 in the genome database which contains one or more genome keys 240 associated with respective genome data 245, typically one for each patient. Each genome key 240 and genome data 245 is uniquely associated with a patient.

Figure 9B:
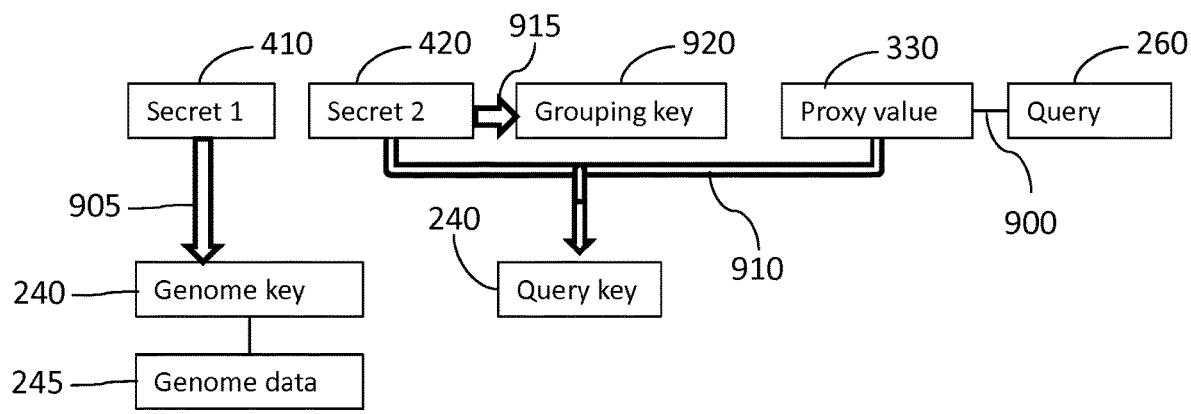
Figure 9C:
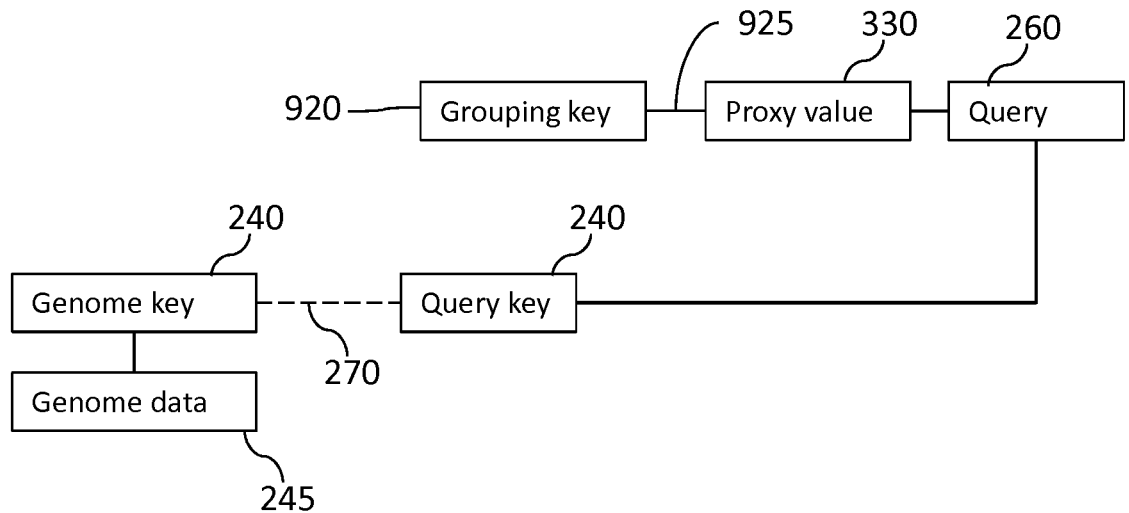
Figure 9D:
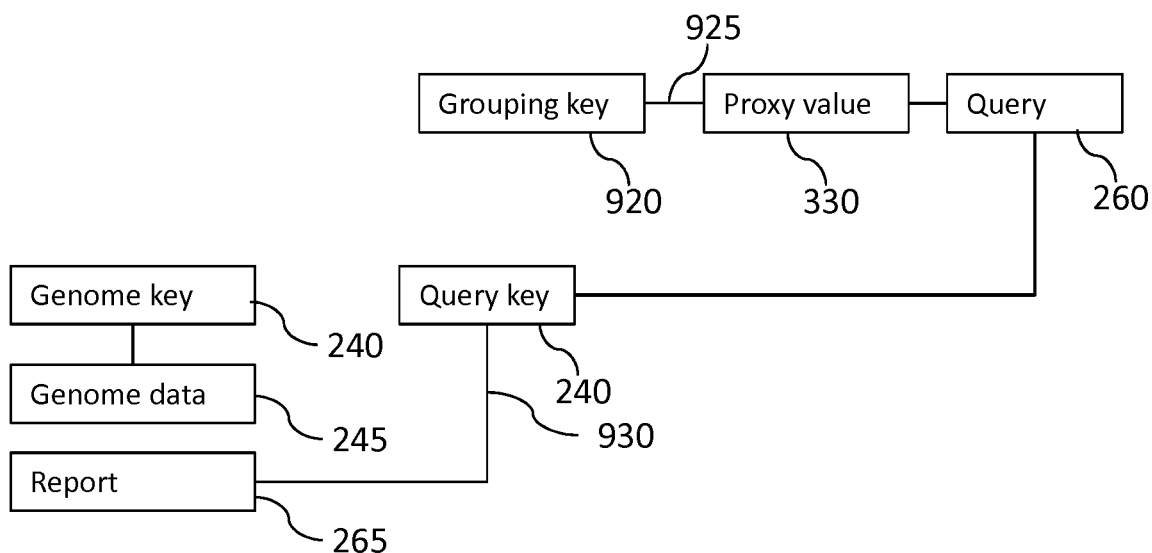

The server 160 then associates a proxy value 330 that is unique to the query request with the query request 255 by way of an association 900 between the proxy value 330 and the query request 255, as illustrated in FIG. 9b. In some embodiments, the proxy value 330 is pre-generated before receipt of the query request 255. In some embodiments, the server 160 generates or selects the proxy value 330 in response to receipt of the query request 255 by assigning universally unique identifiers. Subsequently, the server 160 applies a first one-way function 905 to the first secret 410 to generate the genome key 240 (see FIG. 9b). Since the genome data 245 is associated uniquely with this genome key 240, as described above, the genome data 245 belonging to the patient is found in this way using the first secret 410.

The server 160 also applies a second one-way function 910 to a combination of the second secret 420 and the proxy value 330 to generate the query key 250 and the server 160 applies a third one-way function 915 to the second secret 420 to generate a grouping key 920 (see FIG. 9b). The server 160 then creates an association 925 between the grouping key 920 and the proxy value 330. In this way, the grouping key 920 is uniquely associated with the physician and, by associating the proxy value 330 and hence the query key 250 with the grouping key 920, the physician can later access his or her queries, as described below (see FIG. 9c). Typically, a plurality of proxy values 330 (and hence query requests 255 by the same physician, for his or her patients) will be associated with each grouping key 920. The server 160 creates the temporary link 270 between the query key 250 and the genome key 240 and stores the temporary link 270 in the database, in a way so that it can later be deleted.

As for step 611 described above, subsequent to storing the temporary link 270, the server 160 deletes the first secret 410 and the second secret 420 subsequent to generating the genome key 240 and the query key 250. In some embodiments, the server 160 deletes the first secret 410 and the second secret 420 at the end of the first communications session. Once the first secret 410 and second secret 420 are deleted, it is no longer possible to trace back to the physician and patient, since the generated keys are linked to the secrets by one-way functions.

Similar to step 612, to process the genome query, the server 160 identifies the genome data 245 using the genome key 240. Thus, by way of the temporary link 270 created between the query key 250 and the genome key 240; the genome data 245 is identified for running the query 260 of the query request 255 on it (see 9d). Similar to steps 613 and 615 described above, the query 260 is then processed and once it is no longer needed, the temporary link 270 is deleted.

Figure 10A:
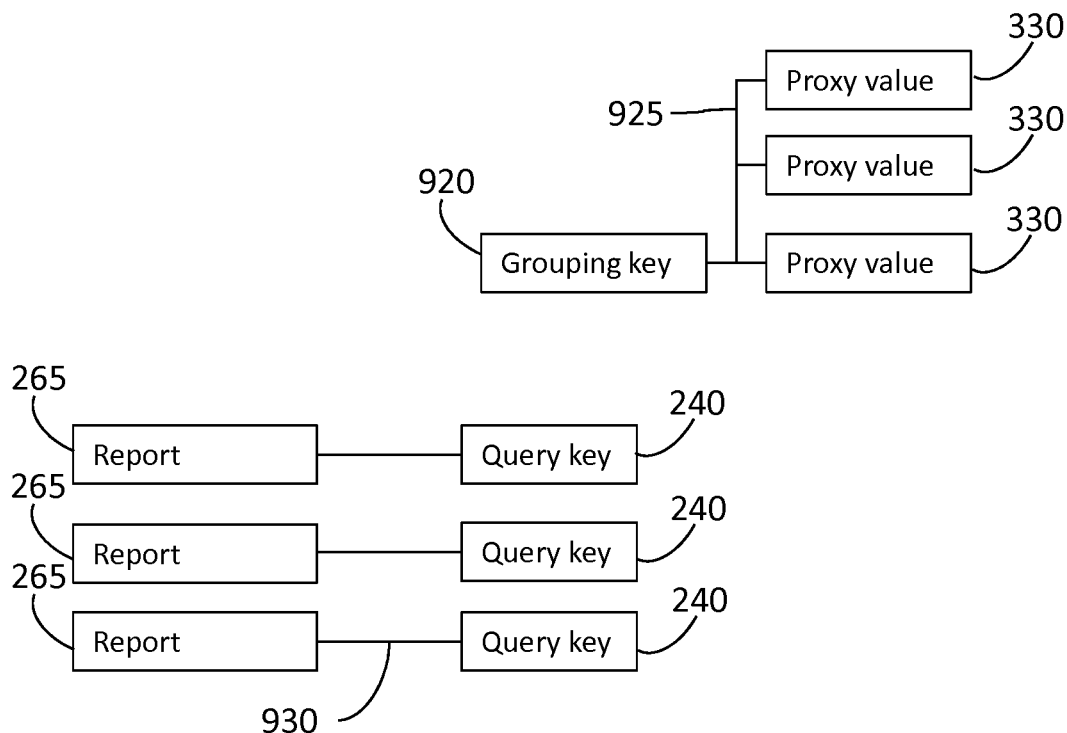
FIGS. 10a-10h illustrates a process for providing report summaries and selected reports in embodiments using one-way functions for combined key generation and identification.

As for the embodiments described above, after one or more first communications sessions, the database of the server 160 comprises one or more reports 265 and one or more query keys 240 associated by way of respective associations 930 in the database. The state of the information stored in the database in embodiments using one-way functions for combined key generation and identification is illustrated in FIG. 10a. The database additionally comprises the grouping key 920 associated with the physician and one or more proxy values 330 corresponding to the one or more query requests 255 and reports 265 associated with the grouping key 920 by associations 925. Thus, the reports are ready for collection as will now be described.

Figure 10B:
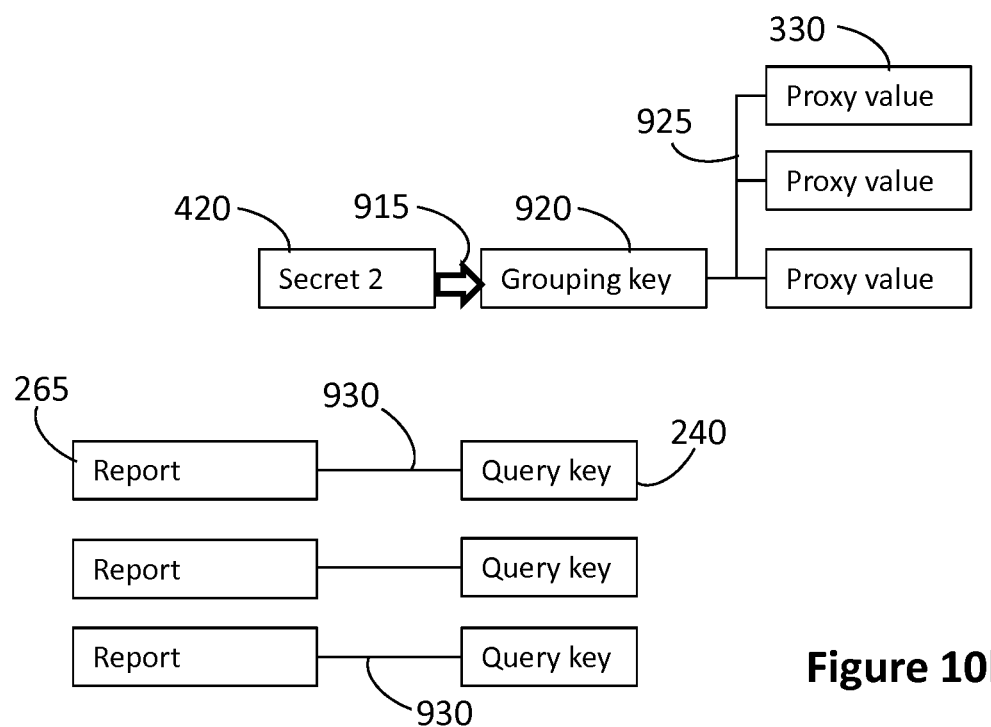
Figure 10C:
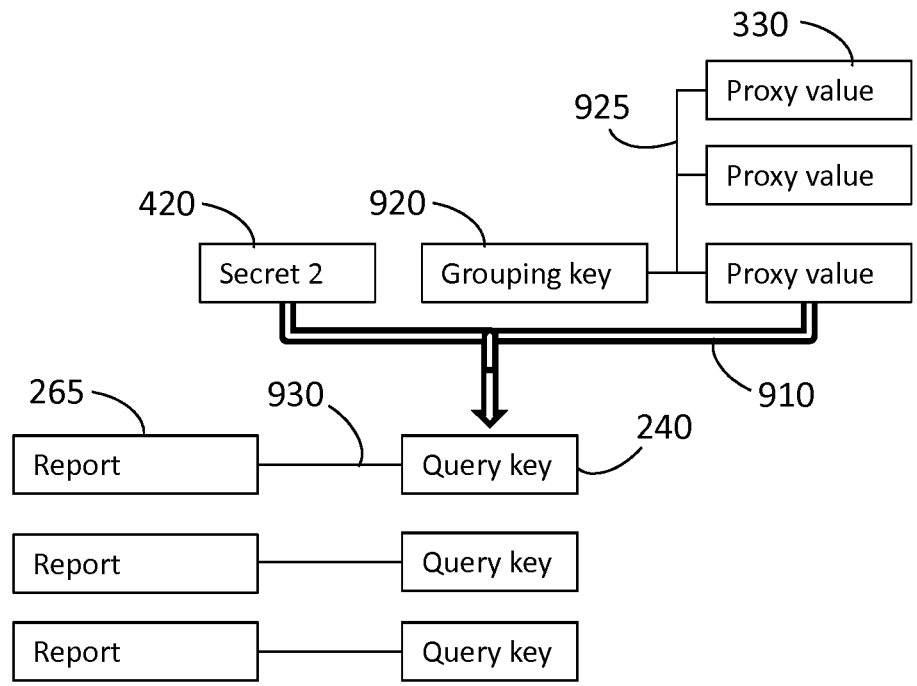
Figure 10D:
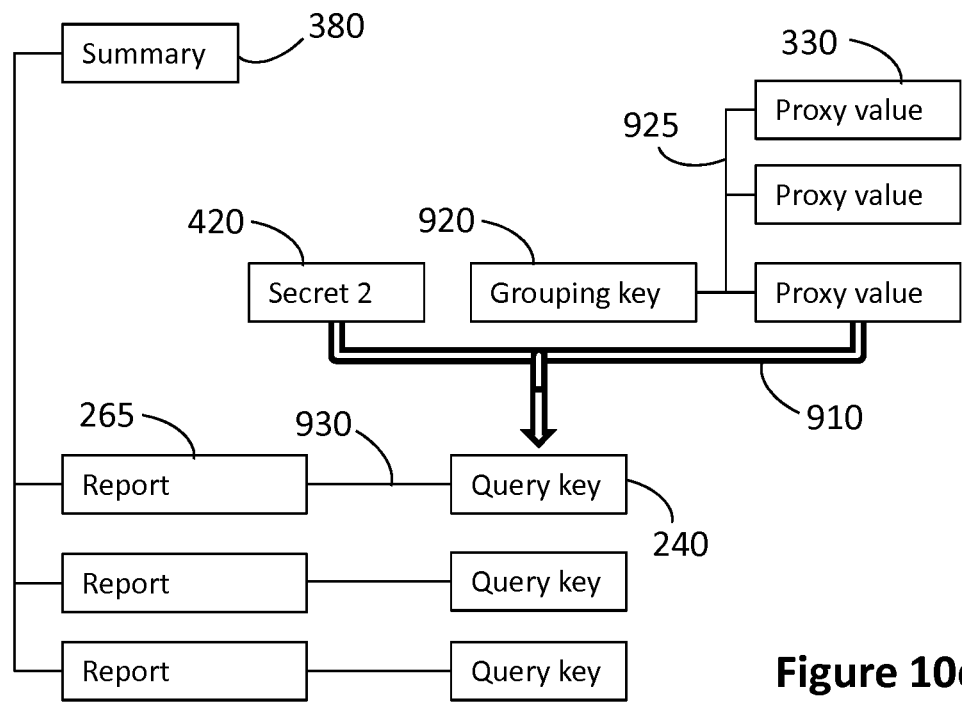
Figure 10E:
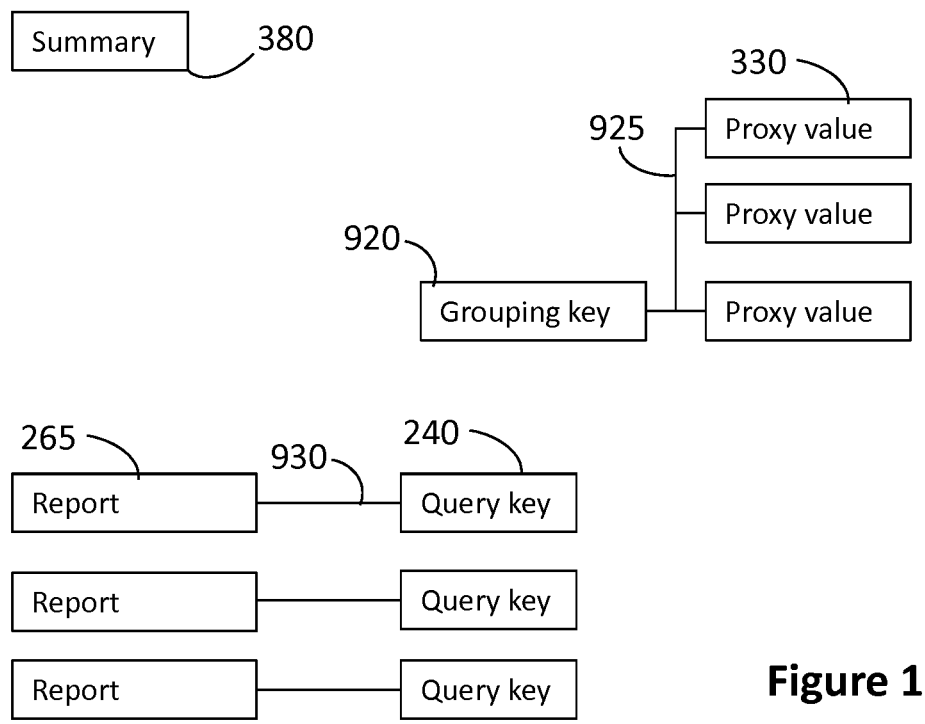
Figure 10F:
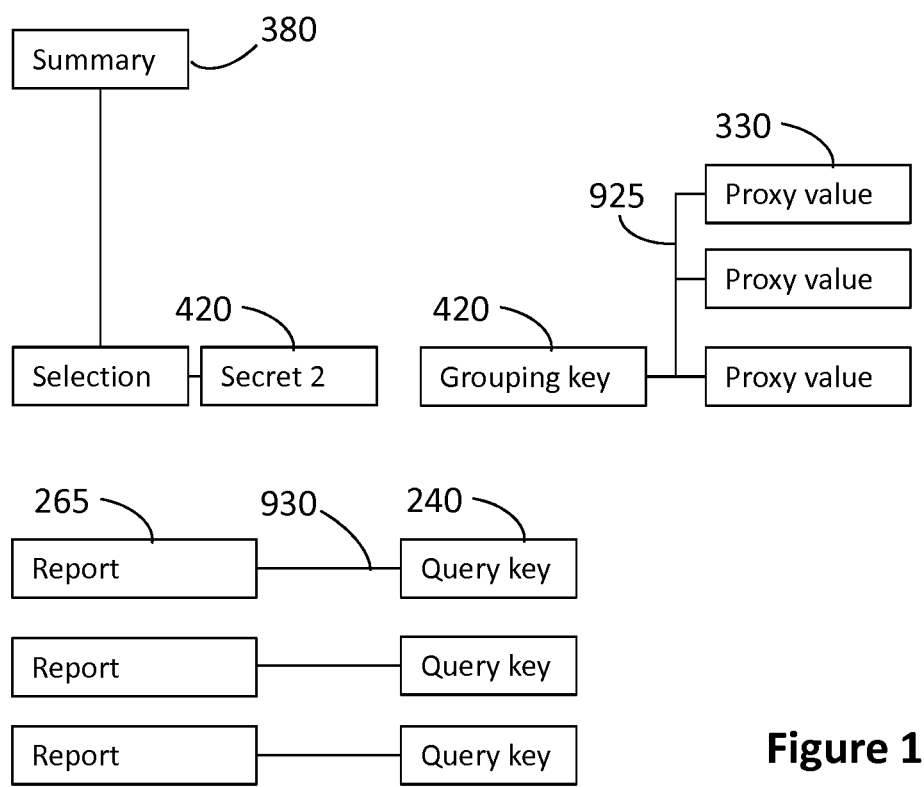
Figure 10G:
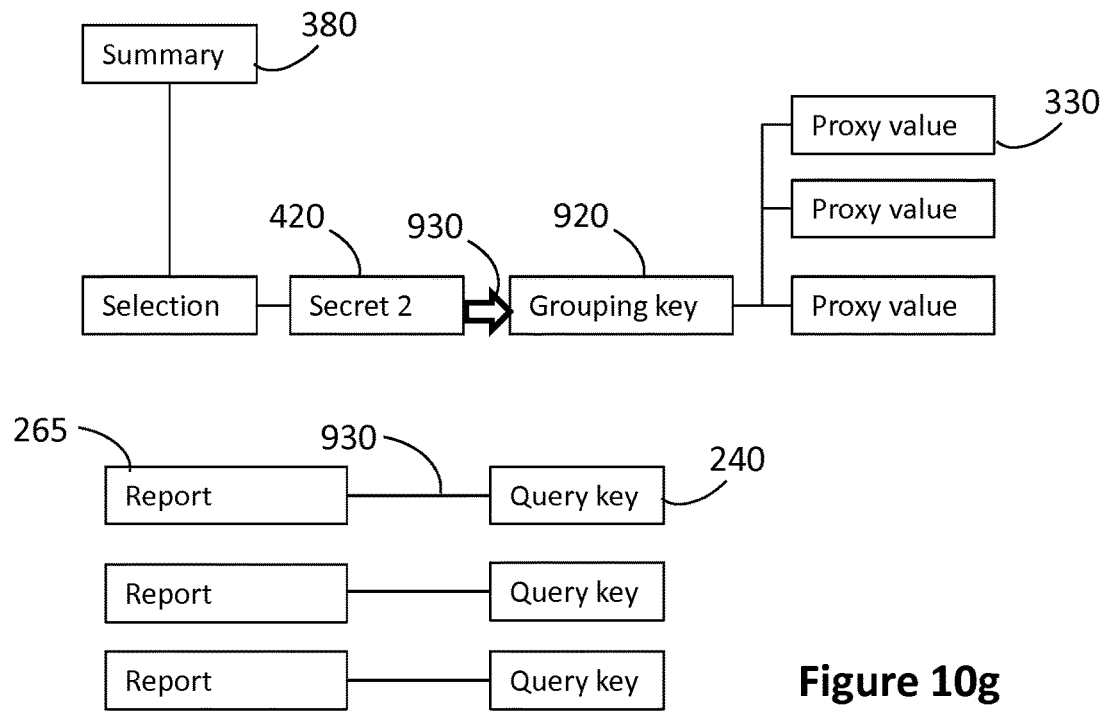

With reference to the process described in FIG. 7, embodiments using one-way functions for combined key generation and identification replace steps 703, 704 with the following process. On receipt of the second secret, the server 160 applies the third one-way function 915 to the second secret 420 to generate the grouping key 920. The state of the information stored in the database at this point is illustrated in FIG. 10b. The server 160 then identifies the one or more proxy values 330 associated with the grouping key 920 by way of associations 925 and applies the second one-way function 910 to a combination of the second secret 420 and the identified one or more proxy values 330. In this way, the server 160 generates one or more query keys 240, each associated with a report 265 by way of the association 930 (see FIG. 10c). Using the generated query keys 240, the server 160 identifies query summary information 380 associated with respective reports 265 associated with the respective one or more query keys 240 (see 10d). The server 160 then deletes the second secret 420 (see FIG. 10e) and sends the query summary information 380 over the communications network 180 to the client computer 130.

At the client side, steps 705 to 707 are equally applicable to the embodiments using one-way functions for combined key generation and identification. Similarly to step 708, the server 160 then receives both the second secret 420 and the selection associated with the query summary information 380 (see FIG. 10f). Subsequently, the server 160 applies the third one-way function 915 to the second secret 420 to generate the grouping key 920. Using the generated grouping key 920, the server 160 identifies one or more proxy values 330 associated with the grouping key 920 by way of the associations 925 (see FIG. 10g).

Figure 10H:
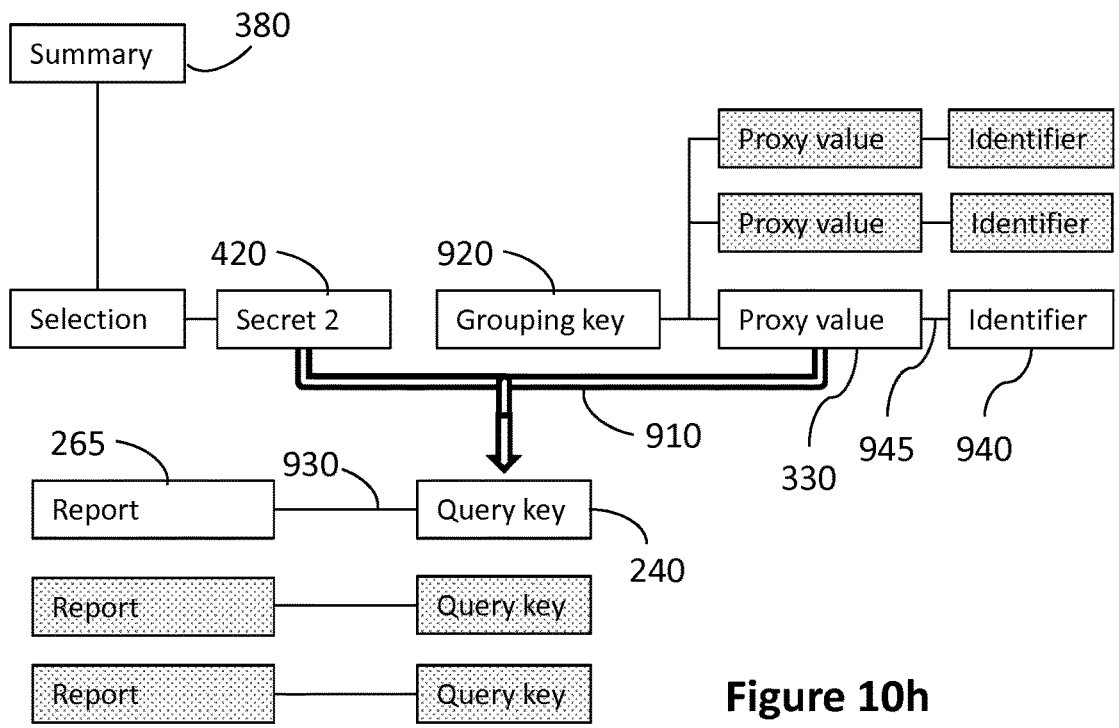

To facilitate report retrieval, in some embodiments, each report 265 identified in the query summary information 380 is associated with a corresponding identifier 940 (see FIG. 10h). The server 160 stores an association 945 between the identifier 940 and the proxy value 330 corresponding to the report 265 to enable the retrieval of the report 265. The client computer 130 receives the identifiers 940 together with the query summary information 380 and sends the corresponding identifier 940 to the server 160 over the communications network 180 when the physician makes the selection. The server 160 then can identify the proxy value 330 corresponding to the identifier 940 using the association 945.

Similar to step 709, the server 160 identifies the proxy value 330 associated with the selected query request 255 or report 265 but then applies the second one-way function 910 to a combination of the second secret 420 and the identified proxy value 330 corresponding to the selection to generate the corresponding query key 240 (see FIG. 10h). Since the generated query key 240, by definition, corresponds to the selected report 265, the server 160 identifies the corresponding report 265 using the association 930, similar to step 710 above. As this is no longer needed the server 160 then deletes the second secret 420, to safeguard privacy and sends the report 265 corresponding to the selection to the client 130 for review by the physician, analogous to steps 711 and 712 described above.

Similar to the embodiments described above, it may be desirable to provide access to the generated reports to the patient in addition to or instead of the physician. This may be achieved by generating a patient grouping key from the first secret 410 and associating the proxy values 330 of query reports 265 generated for the patient (using the first secret 410) with this patient grouping key. Using processes described above, replacing the grouping key 920 with a patient grouping key and the second secret 420 with the first secret 410, the patient can be enabled to access his or her reports 265.

The above description of embodiments using one-way functions for combined key generation and identification has focused on query generation and report retrieval. Naturally, prior to these processes, the database has to be populated with genome data. The process, and its variations, described above with reference to FIG. 8 is equally applicable to these embodiments, with omission of steps 805 and 806 relating to the generation of the genome verification key and noting that the genome key must be generated from the first secret using the first one-way function (i.e. the same one-way function used to generate the genome key for data retrieval/ association). In other words, the genome key must be generated for these embodiments from the first secret using a fixed one-way function that is later also used for generation of the genome key for association and retrieval, that is without a varying random seed as described above in the context of FIG. 8. Further, naturally, the genome key cannot simply be pre-generated but must be specific to the first secret.

While the present system has been designed with anonymity and privacy in mind, it may sometimes be necessary or desirable to contact the patient (the owner of the genome). One example of this occurs in embodiments, where a message is sent to the patient, for example by email, each time the first secret 410 is processed to access a genome. To reconcile this with maintenance of privacy and anonymity, in some embodiments, a fourth one-way function is used. Specifically, in some embodiments, the server 160 applies a fourth one-way function to the first secret 410 to generate a contact key in response to receipt of the first secret 410. The contact key is associated with contact information held in the database for the patient. To this end, contact information is stored in the patient profile 210 and may comprise any one or more of an email address, a telephone number or any other means for contacting the owner of the first secret 410. With this information, the server 160 sends over the communications network 180 a message to the patient in response to receipt of the first secret 410. The message may comprise any one or more of an email notification, a mobile phone notification, a voicemail, SMS message or any other means of notifying the owner of the first secret 410. In this way, misuse of the first secret 410 is easier to detect, while at the same time ensuring anonymity, since the contact information is associated with the contact key, which cannot be traced back to the patient or access data stored in the database. It will be understood that the contact key (or a similar key) can be used to associate contact information and/or other personal data with the first secret for purposes other than that described above.

While a number of different embodiments have been described, some with reference to FIGS. 2 to 8, others with reference mainly to FIGS. 9 and 10, it will be appreciated that the various processes can be combined and that features from either set of embodiments can be added in the other. For example, the use of verification keys described above can be combined with the concept of grouping keys and specific one-way functions to generate and identify keys (or strings specific to the functions), and can be stored in user profiles. Thus, various combinations are possible and herewith disclosed. Also, in all embodiments described herein, reference to private and anonymous portions of the database may refer to physical portions, for example separate servers or drives, or may be logical or even merely conceptual distinctions for the sake of description, rather than physically distinct portions. It will further be understood that associations in the database as referred to herein may be explicit, storing a link to an item of data with the one associated with it, or implicit by storing the associated items of data together, for example in the same row of the database.

The above embodiments rely on several one-way functions to generate various keys from the first secret 410 and second secret 420. The one-way functions may be of any type, as long as it is practically impossible to infer the input from the output (pre-image resistance). The strength of the anonymity protection afforded by the above embodiments depends on the strength of the one-way functions used. In some embodiments, in particular embodiments using one-way functions for combined key generation and identification, a common one-way function is used by the various one-way functions, which are distinguished by respective strings with which the function inputs get concatenated before being applied to the common one-way function to generate an output. Specifically, in some embodiments a 64-character alphanumeric string is used. In particular in the context of embodiments using one-way functions for combined key generation and identification, the string for each one-way function is, for example, randomly generated but is then held constant to ensure consistent computations of the various keys from the first and second secrets, as the case may be.

Having read the above specific description of some example embodiments, the skilled person will be aware that using combinations, modifications and juxtapositions of the above features and embodiments are possible and are covered by the scope of the appended claims, which are not limited to the specific examples described above. For example, although process steps have been described in a certain order, the order can vary from embodiment to embodiment to the extent that the necessary information is available for each step when needed.

The invention claimed is:

1. A method of processing a query on a genome to produce a report, the method comprising:
   receiving a first secret, a second secret and a query request over a communications network during a first communications session and storing a proxy value associated with the query request in a database;
   using the first secret to determine a genome key enabling access to genome data stored in the database and associated with the first secret;
   associating the proxy value and a query key using the second secret such that the query key can only be found with the proxy value using both the proxy value and the second secret;
   storing an association between the genome key and the query key in the database;
   deleting the first and second secrets subsequent to determining the genome key and associating the proxy value and query key during or at the end of the first communications session;
   identifying the genome using the genome key and applying a query associated with the query request to the identified genome to generate a report;
   storing the report in the database in association with the query key, whereby the report can be accessed in the database using the query key; and
   subsequent to storing the report, deleting the association between the genome and query keys.

2. The method of claim 1, wherein determining the genome key using the first secret comprises evaluating a function combining a candidate genome key in the database with the first secret and comparing the result with a genome verification key associated with the first secret to find a match between the result and the verification key, optionally wherein the function combining the candidate genome key with the first secret is a one-way function and optionally wherein the genome verification key is stored in a user profile accessible with credentials including the first secret.

3. The method of claim 1, wherein associating the proxy value and query key comprises computing a query verification key as a function combining the proxy value, query key and second secret and storing the query verification key in the database, optionally wherein the function combining the proxy value, the query key, and the second secret is a one-way function and optionally wherein the query verification key is stored in a user profile accessible with credentials including the second secret.

4. The method of claim 1, wherein the proxy value is generated or selected in response to receipt of the query request.

5. The method of claim 1 comprising receiving the second secret over a communications network during a second, subsequent communications session;
   using the second secret and the proxy value to determine the query key;
   deleting the second secret subsequent to determining the query key during or at the end of the second communications session;
   identifying the report using the query key;
   and sending the report over the communications network during the second communications session.

6. The method of claim 3, comprising receiving the second secret over a communications network during a second, subsequent communications session;
   using the second secret and the proxy value to determine the query key;
   deleting the second secret subsequent to determining the query key during or at the end of the second communications session;
   identifying the report using the query key;
   and sending the report over the communications network during the second communications session;
   wherein determining the query key using the second secret and proxy value comprises evaluating the function combining the proxy value, query key and second secret for a candidate query key in the database and comparing the result with the query verification key to find a match between the result and the query verification key.

7. The method of claim 5 comprising storing a plurality of proxy values in the database so that they are accessible using credentials including the second secret, and further comprising, during the second communication session, receiving a user selection of a report to be retrieved, wherein the proxy value used to determine the query key corresponds to the selected report to be retrieved.

8. The method of claim 1, wherein the first secret is associated with a patient and, wherein the second secret is associated with a physician.

9. The method of claim 1, the method comprising retrieving contact information and transmitting a message using the retrieved contact information indicating that the first secret has been used to access the genome data.

10. The method of claim 2, comprising retrieving contact information and transmitting a message using the retrieved contact information indicating that the first secret has been used to access the genome data, wherein the contact information is stored in association with the genome verification key, optionally in a user profile accessible with credentials including the first secret.

11. A method of populating a genomic database, the method comprising:
receiving a first secret over a communications network during a communications session;
using the first secret and a genome key to generate a genome verification key associated with the first secret and the genome key, whereby the genome key can be matched with the genome verification key only using both the first secret and the genome verification key;
sending the genome key over the communications network to enable it to be associated with a genome sequenced by a genome provider; and
deleting the first secret subsequent to generating the genome verification key during or at the end of the communications session,
the method optionally further comprising
receiving genome data together with the genome key; and
storing the genome data in the database in association with the genome key.

12. A system for processing a query on a genome to produce a report, the system comprising a database and a processor, wherein the processor is configured to:
receive a first secret, a second secret and a query request over a communications network during a first communications session and store a proxy value associated with the query request in a database;
use the first secret to determine a genome key enabling access to genome data stored in the database and associated with the first secret;
associate the proxy value and a query key using the second secret such that the query key can only be found with the proxy value using both the proxy value and the second secret;
store an association between the genome key and the query key in the database;
delete the first and second secrets subsequent to determining the genome key and associating the proxy value and query key during or at the end of the first communications session;
identify the genome using the genome key and applying a query associated with the query request to the identified genome to generate a report;
store the report in the data base in association with the query key, whereby the report can be accessed in the database using the query key; and
subsequent to storing the report, delete the association between the genome and query keys.

13. The system of claim 12, wherein determining the genome key using the first secret comprises evaluating a function combining a candidate genome key in the database with the first secret and comparing the result with a genome verification key associated with the first secret to find a match between the result and the verification key, optionally wherein the function combining the candidate genome key with the first secret is a one-way function and optionally wherein the genome verification key is stored in a user profile accessible with credentials including the first secret.

14. The system of claim 12, wherein associating the proxy value and query key comprises computing a query verification key as a function combining the proxy value, query key and second secret and storing the query verification key in the database, optionally wherein the function combining the proxy value, query key and second secret is a one-way function and optionally wherein the query verification key is stored in a user profile accessible with credentials including the second secret.

15. The system of claim 12, wherein the proxy value is generated or selected in response to receipt of the query request.

16. The system of claim 12, wherein the processor is configured to:
receive the second secret over a communications network during a second, subsequent communications session;
use the second secret and the proxy value to determine the query key;
delete the second secret subsequent to determining the query key during or at the end of the second communications session;
identify the report using the query key; and
send the report over the communications network during the second communications session.

17. The system of claim 14, wherein the processor is configured to:
receive the second secret over a communications network during a second, subsequent communications session;
use the second secret and the proxy value to determine the query key;
delete the second secret subsequent to determining the query key during or at the end of the second communications session;
identify the report using the query key; and
send the report over the communications network during the second communications session, and wherein determining the query key using the second secret and proxy value comprises evaluating the function combining the proxy value, query key and second secret for a candidate query key in the database and comparing the result with the query verification key to find a match between the result and the query verification key.

18. The system of claim 16, wherein the processor is configured to store a plurality of proxy values in the database so that they are accessible using credentials including the second secret and wherein the processor is configured to receive, during the second communication session, a user selection of a report to be retrieved, wherein the proxy value used to determine the query key corresponds to the selected report to be retrieved.

19. The system of claim 12, the processor being configured to retrieve contact information and transmit a message using the retrieved contact information indicating that the first secret has been used to access the genome data.

20. A system for populating a genomic database, the system comprising a database and a processor configured to:

receive a first secret over a communications network during a communications session;

use the first secret and a genome key to generate a genome verification key associated with the first secret and the genome key, whereby the genome key can be matched with the genome verification key only using both the first secret and the genome verification key;

send the genome key over the communications network to enable it to be associated with a genome sequenced by a genome provider; and delete the first secret subsequent to generating the genome verification key during or at the end of the communications session, the processor optionally being further configured to receive genome data together with the genome key; and store the genome data in the database in association with the genome key.

* * * * *